US009758808B1

(12) United States Patent
Maye et al.

(10) Patent No.: US 9,758,808 B1
(45) Date of Patent: Sep. 12, 2017

(54) BIOLUMINESCENCE RESONANCE ENERGY TRANSFER BETWEEN BIOLUMINESCENT PROTEINS AND SEMICONDUCTIVE NANOMATERIALS

(71) Applicants: Mathew Maye, Binghamton, NY (US); Rabeka Alam, Syracuse, NY (US)

(72) Inventors: Mathew Maye, Binghamton, NY (US); Rabeka Alam, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 32 days.

(21) Appl. No.: 14/073,463

(22) Filed: Nov. 6, 2013

Related U.S. Application Data

(60) Provisional application No. 61/722,977, filed on Nov. 6, 2012.

(51) Int. Cl.
*A61K 49/00* (2006.01)
*C12Q 1/66* (2006.01)

(52) U.S. Cl.
CPC ............... *C12Q 1/66* (2013.01); *A61K 49/00* (2013.01); *A61K 49/0013* (2013.01); *C12Q 2521/543* (2013.01)

(58) Field of Classification Search
None
See application file for complete search history.

(56) References Cited

U.S. PATENT DOCUMENTS 8,263,417 B2 * 9/2012 Rao et al. ................. 436/518

OTHER PUBLICATIONS

Alam, Rabeka; et al; "Designing Quantum Rods for Optimized Energy Transfer with Firefly Luciferase Enzymes" Nano Letters, 12, 3251-3256, 2012.*
Yong, Ken-Tye; et al; "Quantum Rod Bioconjugates as Targeted Probes for Confocal and Two-Photon Fluorescence Imaging of Cancer Cells" Nano Letters, 7, 761-765, 2007.*

* cited by examiner

*Primary Examiner* — David Berke-Schlessel
(74) *Attorney, Agent, or Firm* — Bond Schoeneck & King, PLLC; David Nocilly; George McGuire

(57) ABSTRACT

A bioluminescence energy transfer (BRET) nanosystem having semiconductive quantum rods (QRs) bound by firefly luciferase *Photinus pyralis* (Ppy) for improved conversion of chemical energy to light, such as in solid-state lighting, near-infrared imaging systems, and in vivo infrared imaging. The nanosystems are formed by synthesizing CdSe/CdS or CdSe/CdS/ZnS quantum rods, rendering the dots hydrophilic and colloidally stable with a facile His-capping, incubating with a Ppy variant (PpyGRTS) at increasing loading ratios, and adding an excess of the luciferin (LH2) substrate to the PpyGRTS-QRs.

18 Claims, 19 Drawing Sheets

BIOLUMINESCENCE RESONANCE ENERGY TRANSFER BETWEEN BIOLUMINESCENT PROTEINS AND SEMICONDUCTIVE NANOMATERIALS

CROSS-REFERENCE TO RELATED APPLICATIONS

The present application claims priority to U.S. Provisional Application No. 61/722,977, filed on Nov. 6, 2012.

STATEMENT OF FEDERALLY SPONSORED RESEARCH

This invention was made with government support under Grant No. FA9550-10-1-003 awarded by the Air Force Office of Scientific Research. The government has certain rights in the invention.

BACKGROUND OF THE INVENTION

1. Field of the Invention

The present invention relates to nanoscale energy transfer, the conversion of chemical energy into light and, more particularly, to semiconductive quantum rods that posses rod-in-rod morphology that are conjugated with firefly luciferase.

2. Description of the Related Art

Research at the nanoscale biotic-abiotic interface centers on endowing an inorganic nanocrystal with the physical, chemical, or energetic properties of biosystems. This has led to an influx of biomimetic self-assembly, recognition, and energy transfer designs. One frontier that combines these advances is the ability to harness the energy converting properties of enzymes, by effectively transferring chemical energy from a substrate to an inorganic nanomaterial. This process could lead to revolutionary ways of converting chemical energy to light, for example, providing new lighting strategies, in-vivo signaling routes, and improved understanding of biosystems.

Quantum dots and rods have been proven to be powerful energy donors in a number of fluorescence resonance energy transfer (FRET) designs. This is due in large part to a broad absorption profile, size tunable emission, photostability, and long excited state lifetimes. However these same qualities limit the use of QDs as energy acceptors.

Bioluminescence energy transfer (BRET) on the other hand utilizes a bioluminescent enzyme in the presence of substrate to generate an excited state donor, and a fluorescent protein, dye, or QD 11-15 as the acceptor. For example, bioluminescent enzymes mutated from *R. reniformis* luciferase (Luc8) can be conjugated to semiconductive quantum dots (QDs) via EDC coupling. In the presence of the substrate colenterazine, the QD accepts the excited state energy of Luc8 via the non-radiative pathway known as bioluminescence resonance energy transfer (BRET). This allows for the blue-green emission of the enzyme to be converted to the red, and even near infrared (NIR) colors of the QD. BRET nanosystems have been used for in-vivo NIR imaging, where it has proven to be particularly useful due to low background signals and the lack of a direct excitation requirement. The metric for BRET efficiency is the BRET ratio (BR), where the emission of the acceptor and donor are compared. To date, typical BR using QD acceptors is limited to only 0.5~2.0. This efficiency is much lower than comparable studies using fluorescent protein (BR=1~4), or molecular fluorophore acceptors (BR=10~14). The origins of the comparatively low BR with QDs is unknown, but may likely be due to relatively large spatial distances (r), as well as limited stoichiometry (n).

Due to the microsecond lifetimes of bioluminescent processes and the chemical origin of excitation, the QD in particular are ideal acceptors due to shorter lifetimes and broad absorption in the visible region. To date, QD based BRET nanosystems use blue-emitting *R. reniformis* luciferase (rLuc) expressed with multiple copies of surface exposed lysine residues, which were conjugated to free carboxylates at polymer wrapped QDs. BRET was observed for a number of QD colors, including near infrared emitters, which have proven to be particularly useful for in-vivo imaging. There remains an important need to improve BRET efficiency by tailoring of QD morphology and structure to better optimize and understand the BRET nanosystems.

BRIEF SUMMARY OF THE INVENTION

The present invention comprises a BRET nanosystem having semiconductive quantum rods (QRs) bound by firefly luciferase *Photinus pyralis* (Ppy) using a direct bio-attachment capability. Ppy-QR BRET nanosystems according to the present invention routinely achieve BR up to 44. The present invention thus increases the energy transfer efficiency of know systems up to 88-fold, and thus allows for improved conversion of chemical energy to light. The present invention may be used for solid-state lighting, near-infrared imaging (i.e., night vision) systems, and in vivo infrared imaging.

Ppy-QR BRET nanosystems are formed by synthesizing CdSe/CdS or CdSe/CdS/ZnS quantum rods (QRs) via organometallic routes, resulting in trioctylphosphine oxide (TOPO) and alkylphosphonic acid (PA) capped QRs in chloroform. Next, the QRs undergo phase transfer and ligand exchange with Lhistidine (His), which renders the dots hydrophilic and colloidially stable with a facile His-capping, the excess of which is removed via purification. The His-QRs are then incubated with PpyGRTS at increasing loading ratios, L=[PPy]:[QR]. Due to the N-terminus 6×His modification of this PpyGRTS, it binds to the QR interface, displacing the His monolayer. Next, an excess of the luciferin (LH2) substrate is added to the PpyGRTS-QRs, which immediately induces bioluminescence from PpyGRTS, and bioluminescence resonance energy transfer (BRET) to the QR.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1(a) through (e) are a series of schematics showing the synthesis and operation of the present invention along with a representative set of TEM micrographs of PpyGRTS-QR(675) conjugates according to the present invention;

FIGS. 2(a) and (b) are micrographs of CdSe/CdS QR(675) and CdSe/CdS/ZnS QR(675*) according to the present invention along with their respective BRET emission profiles;

FIGS. 3(a) and (b) are micrographs of CdSe/CdS QR(628) and CdSe/CdS/ZnS QR(628*) according to the present invention along with their respective BRET emission profiles;

FIGS. 4(a) and (b) are micrographs of CdSe/CdS QR(613) and CdSe/CdS/ZnS QR(613*) according to the present invention along with their respective BRET emission profiles;

FIGS. 5(a) through (d) are graphs of BRET efficiency plots for PpyGRTS donors and QR acceptors, the BR measured with respect to aspect ratio at L=5 and 10 for CdSe/CdS and CdSe/CdS/ZnS QRs, and a series of schematics of the microstructure of the particular QRs assessed in connection with the present invention, including dot-in-dot, rod-in-rod, and dot-in-rod types;

FIGS. 6(a) through (b) are schematics of the alkyl-capped QD(800) QDs that were phase transferred by ligand exchange with L-histidine (His), which rendered the QDs hydrophilic and colloidally stable, where (a) shows the his tagged QDs are incubated with PpyGRTS at increasing loading ratios, L=[Ppy]:[QD], between 0.5-40, (b) shows that Due to the N-terminus 6×His modification on PpyGRTS, it binds to the surface of the QDs, displacing the His monolayer, and FIG. 6(c) is a micrograph of Invitrogen QD(800), d=4.0±0.5 nm (c).

FIGS. 7(a) though (f) are representative BRET emission spectra between PpyGRTS and QD(800) at L=[PPyGRTS]:[QD(800)]=0.5 (a), 1.0 (b), 2.0 (c), 5.0 (d), and 10 (e), with a bar graph summarizing measured BR dependence on L(f);

FIGS. 8(a) and (b) are graphs of the QD(800) and PPyGRTS spectral properties and the calculated BRET efficiency plot with idealized PpyGRTS-QD(800) distances (r).

FIGS. 9(a) through (c) are photographs of bioluminescence of PpyGRTS and BRET between PpyGRTS and QD800 taken with standard digital camera, where FIG. 9(b) is a photograph of bioluminescence of PpyGRTS and BRET between PpyGRTS and QD800 taken with night vision goggles and FIG. 9(c) is a night vision photograph of scaled up BRET using a PDMS mold of a Syracuse University (SU) logo.

FIGS. 10(a) through (c) are: (a) a TEM micrograph and statistical analysis; (b) of CdSe/CdS-QR(613) (l/w=1.8±0.2, l=9.1±0.9 nm, w=5.0±0.4 nm); and (c) a graph of the spectral overlap of QR with PpyGRTS;

FIGS. 11(a) through (c) are: (a) a TEM micrograph and statistical analysis; (b) of CdSe/CdS/ZnS-QR(613*) (l/w=1.9±0.3, l=10.3±1.3 nm, w=5.3±0.5 nm); and (c) a graph of the spectral overlap of QR with PpyGRTS;

FIGS. 12(a) through (c) are: (a) a TEM micrograph and statistical analysis; (b) of CdSe/CdS-QR(628) (l/w=8.7±1.6, l=50.1±5.5 nm, w=5.9±0.8 nm); and (c) a graph of the spectral overlap of QR with PpyGRTS;

FIGS. 13(a) through (c) are: (a) a TEM micrograph and statistical analysis; (b) of CdSe/CdS/ZnS-QR(628*) (l/w=7.4±1.5, l=52.1±5.8 nm, w=7.2±1.1 nm); and (c) a graph of the spectral overlap of QR with PpyGRTS;

FIGS. 14(a) through (c) are: (a) a TEM micrograph and statistical analysis; (b) of CdSe/CdS-QR(675) (l/w=3.1±0.5, l=24.8±3.6 nm, w=8.2±1.3 nm); and (c) a graph of the spectral overlap of QR with PpyGRTS;

FIGS. 15(a) through (c) are: (a) a TEM micrograph and statistical analysis; (b) of CdSe/CdS/ZnS-QR(675*) (l/w=3.0±0.5, l=26.6±3.8 nm, w=9.1±1.3 nm); and (c) a graph of the spectral overlap of QR with PpyGRTS;

FIGS. 16(a) through (h) are representative BRET emission spectra for Ppy-QR(675) (a-d) and Ppy-QR(675*) (e-h) at [Ppy]:[QR]=L=5, 10, 20, 40. The calculated BRET ratios (BR) are shown;

FIGS. 17(a) through (f) are representative BRET emission spectra for Ppy-QR(628) (a-c) and Ppy-QR(628*) (d-f) at [Ppy]:[QR]=L=2, 5, 10. The calculated BRET ratios (BR) are shown;

FIGS. 18(a) through (f) are representative BRET emission spectra for Ppy-QR(675) (a-b) and Ppy-QR(675*) (d-f) at at [Ppy]:[QR]=L=2, 5, 10. The calculated BRET ratios (BR) are shown;

DETAILED DESCRIPTION OF THE INVENTION

Figure 1:
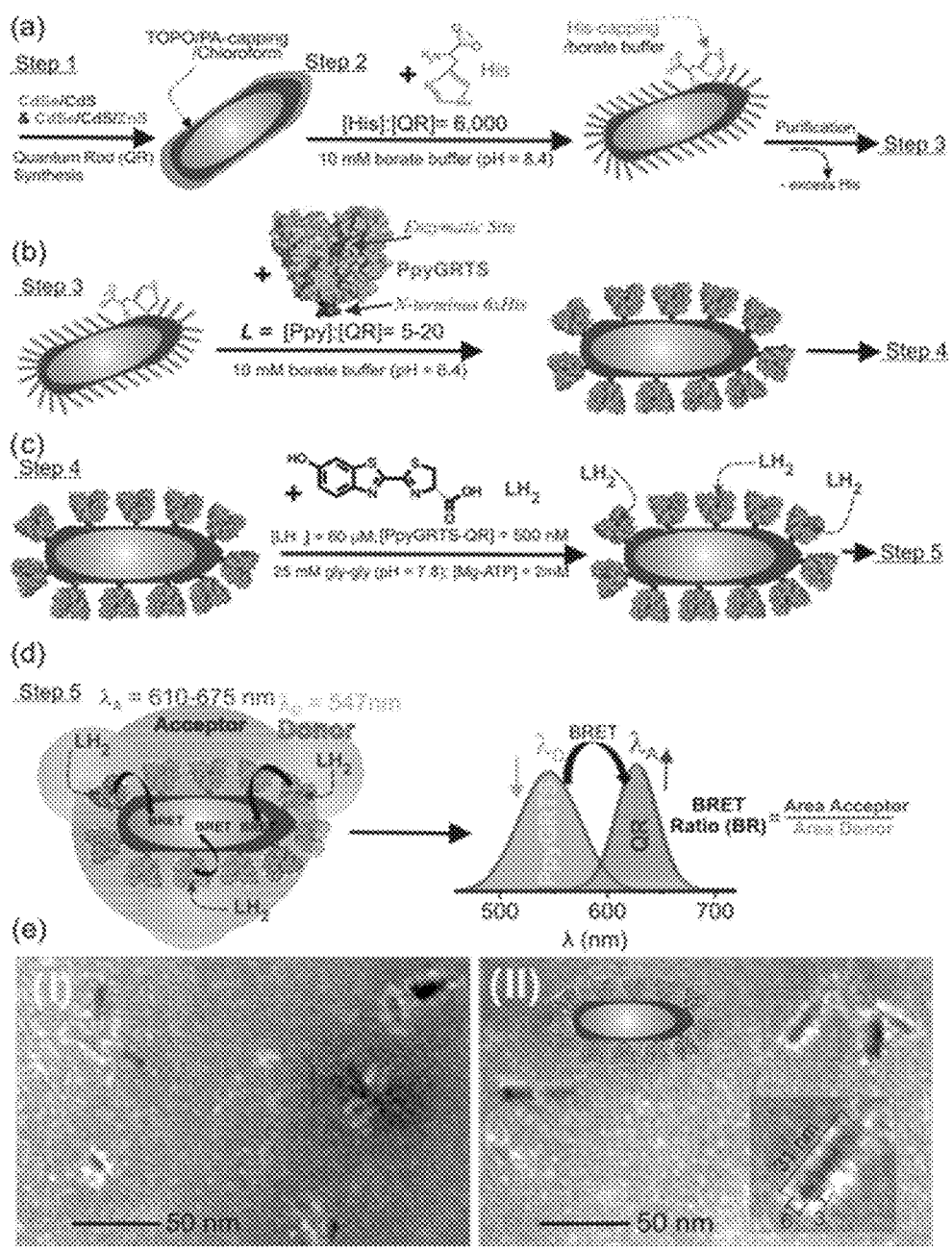

Referring now to the drawings, wherein like reference numerals refer to like parts throughout, there is seen in FIG. 1 a QD BRET nanosystem based on firefly luciferase from *Photinus pyralis* (PPy) and semiconductive quantum rods (QRs). The native and recombinant Ppy luciferases are robust and emit yellow-green light (%=560 nm) at pH=7.8 in the presence of the substrates firefly (beetle) luciferin (LH2), Mg-ATP, and oxygen. The PpyLH2 combination is one of the brightest systems in nature and has one of the highest known quantum yields for luciferases (41±7.4%). CdSe/CdS and CdSe/CdS/ZnS QRs were chosen as BRET acceptors due to long lifetimes (>20 ns), broad absorption, synthetic control of aspect ratio and microstructure, and increased surface area for higher acceptor/donor stoichiometry.

The assembly design and main structural concerns of a biotic-abiotic BRET nanosystem according to the present invention is further shown in FIG. 1. To provide a robust signal approximately half as intense as the wild-type protein, a highly thermostable Ppy variant PpyGRTS was used. The emission spectrum of PpyGRTS is shifted to the blue ($\lambda_D$=546 nm) and is resistant to spectral shifts at high temperature and low pH. The PpyGRTS was directly attached to the QR interface by the N-terminus hexahistidine tag (6×His), which has been shown to coordinate to QDs. This direct attachment was achievable because the as-synthesized hydrophobic-capped QRs were made hydrophilic and colloidally stable via the use of a histidine mediate phase transfer, as seen FIG. 1(a)-(b) and further described herein. This attachment approach allows for the shortest possible donor-acceptor distance. The green emitting PpyGRTS serves as the bioluminescence donor ($\lambda_D$=546 nm) in the presence of LH2 substrates. The QR acceptors are constructed from core/shell designs, where the inner CdSe core serves as the source for emission ($\lambda A$=605-675 nm) that is tailored by novel tuning of the QRs aspect ratios (l/w), which in this study were synthetically modified from 2 to ~7.

Referring to 2(a), BRET was observed between the PpyGRTS donor, and CdSe/CdS QR acceptor with $\lambda A$=675 nm (denoted as QR(675)). The TEM micrograph of the QR(675) revealed an aspect ratio (l/w) of 3.1±0.5 (l=24.8±3.6 nm, w=8.2±1.3 nm). The BRET energy transfer efficiency, BRET ratio (BR), was found to be highly susceptible to the molar loading ratio, L=[PpyGRTS]:[QR]. As seen in FIG. 2(a), the typical BRET emission spectra was at L=5, the characteristic feature of which is the low PpyGRTS donor emission and the presence of a large QR emission. Unlike traditional QR photoluminescence spectra, no direct excitation is present in the system, which serves as an attractive internal control that demonstrates energy transfer from PpyGRTS. After spectral deconvolution, the BR of ≈44.2 at L=5 was calculated based on integration of emission areas. Multiple repeat experiments were performed that resulted in similar efficiencies (±30%). In addition, control experiments in which the PpyGRTS is not assembled at the QR showed no BRET efficiency. Interestingly, a decrease in BR to 32.0, 24.4, and 17.8 was observed despite an increase in L=10, 20, 40, respectively, as seen in the inset of FIG. 2(a). These results suggest that an optimum L exists, possibly because some of the bound PpyGRTS is inactive or linked at distances too great for efficient Förster transfer. These BR values are the highest achieved to date for a BRET nanosystem, and comparable to systems using molecular fluorophores with the highest quantum efficiency closest donor-acceptor distance.

The resonance energy transfer efficiency of a donor/acceptor pair is highly sensitive to center-to-center (dipole-to-dipole) distances. As a morphological control, r was increased by re-processing the CdSe/CdS QR(675) to grow a 0.5 nm thick layer of ZnS, creating CdSe/CdS/ZnS QRs (denoted as QR(675*)). As a result, the QR(675*) have a slightly decreased aspect ratio, l/w=3.0±0.5 (l=26.6±3.8 nm, w=9.1±1.3 nm). Interestingly, this additional layer and larger distance had a significant effect on the BRET response, as seen in FIG. 2(b). For instance, at L=5, a 3.5× decrease in BRET was observed (BR=12.5) compared to the QR(675). Similarly to the QR(675) parent, the system also showed a decreased in BR as L increases. This is likely due to the underlying morphology staying very similar despite the increase in r.

The dependence of QR aspect ratio and L on BRET response was next studied using both longer and shorter QRs. Referring to FIG. 3(a), a TEM micrograph of a longer and narrower CdSe/CdS QR with l/w=8.7±1.6 (l=50.1±5.5 nm, w=5.9±0.8 nm) was examined. Due to the thinner diameter, the QR emitted at $\lambda_A$=628 nm (denoted as QR(628)). This morphology change was achieved by using smaller initial CdSe cores, and tuned growth conditions, as described herein. Compared to the QR(675) shown above, a significant decrease in BR was observed for QR(628). For instance, a BR of 1.2, 1.6, and 0.9 was measured at L=2, 5, and 10, as seen in FIG. 3(a). Similarly to the study above, a ZnS layer was deposited, resulting in an average thickness of ~0.7 nm (l/w=7.4±1.5, l=52.1±5.8 nm, w=7.2±1.1 nm). This resulted in the decrease in BR to 1.4~0.9 for QR(628*), as seen in FIG. 3(b). Surprisingly, these longer QRs with the capability to bind more PpyGRTS did not achieve BR as high as the QR(675).

To further investigate the BR dependence on aspect ratio, CdSe/CdS QRs with smaller aspect ratio than both QR(675) and QR(628) were fabricated. FIG. 4(a) show a TEM micrograph for CdSe/CdS with l/w=2.1±0.3 (l=9.9±0.8 nm, w=4.7±0.4 nm) and $\lambda A$=613 nm (denoted as QR(613)). After identical phase transfer and incubation with PpyGRTS as described above, these QR(613) have stable BR of 0.4~0.3, as seen in FIG. 4(a), with similar values observed for QR(613*) with ZnS shells, as seen in FIG. 4(d).

Figure 2:
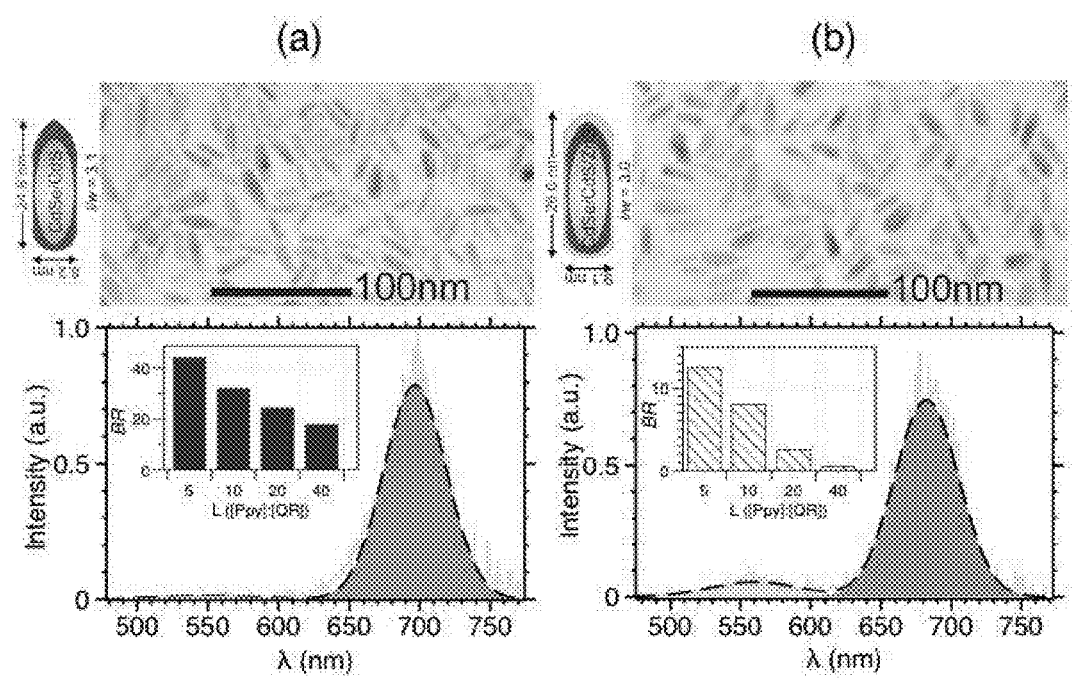
Figure 3:
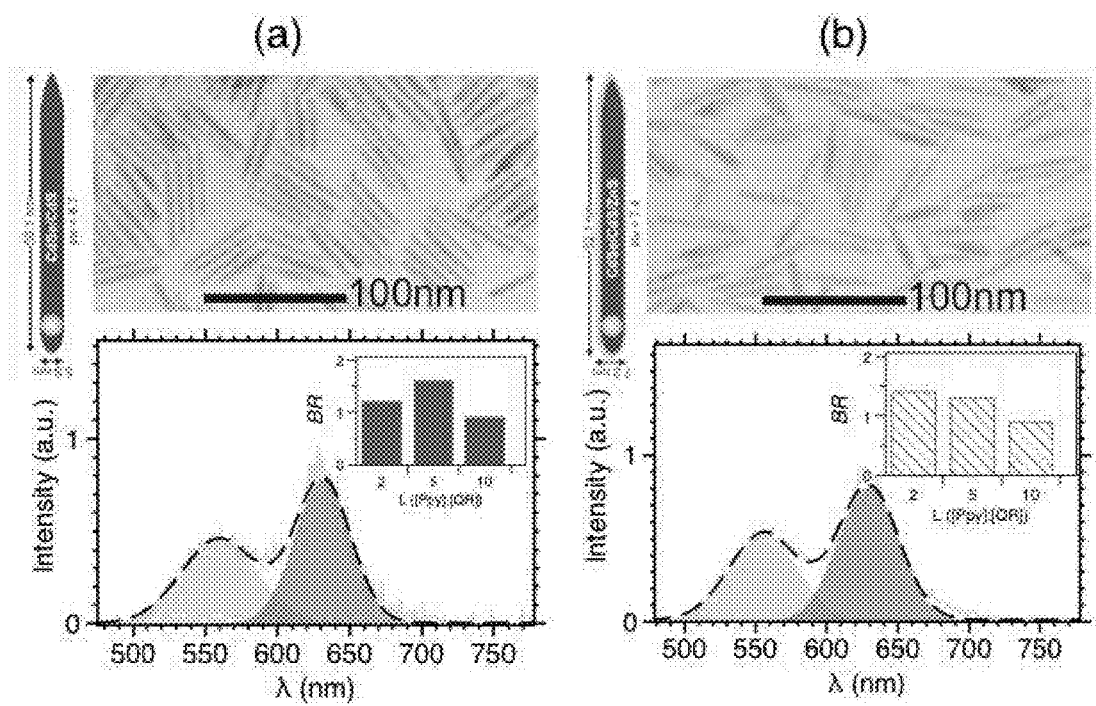
Figure 4:
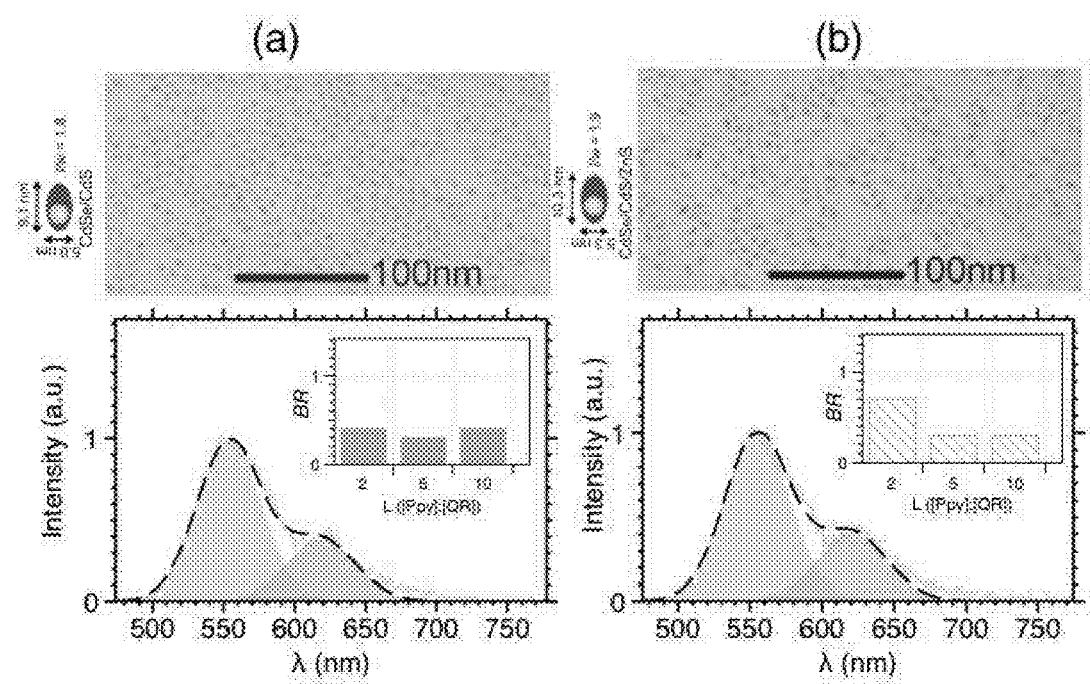

The BRET efficiencies measured in FIGS. 2-4 are the result of both spectral and morphological characteristics of the PpyGRTS-QR nanosystem. For example, because each QR has a different absorption profile, extinction coefficient, and photoluminescence emission, the resonance energy transfer parameters will be different. In BRET, the same resonance energy transfer model is used to that of FRET, were energy transfer efficiency (E) is related to Förster distance (R0) and r by $E=R0^6/R0^6+r^6$. The BRET efficiency plots for the PpyGRTS donor and the CdSe/CdS or CdSe/CdS/ZnS QR acceptors discussed above are seen in FIG. 5(a). A key feature of this calculation is the extended BRET efficiency region for QR(675), that due to a high spectral overlap integral (JQR(675)=1.19×10$^{-11}$M$^{-1}$ cm$^3$), accounts for an exceptionally large Förster distance of R0=9.4 nm, as seen Table 1 below.

TABLE 1

Bioluminscence properties of Ppy measured at pH 7.8

| Enzyme | De-Rise[2] (s) | cay[3] (min) | Relative Activity[1] | | $K_m$ (µM) | | $\lambda_D$ (nm, fwhm)[4] pH 7.8 |
| --- | --- | --- | --- | --- | --- | --- | --- |
| | | | Flash height | Integration (15 min) | LH$_2$ | Mg—ATP | |
| Ppy WT | 0.37 | 0.15 | 100 | 100 | 15 ± 2 | 160 ± 20 | 561 (79) |
| 6xHis-Ppy GRTS | 0.52 | 0.65 | 39 | 100 | 23 ± 3 | 163 ± 27 | 546 (77) |

Figure 5:
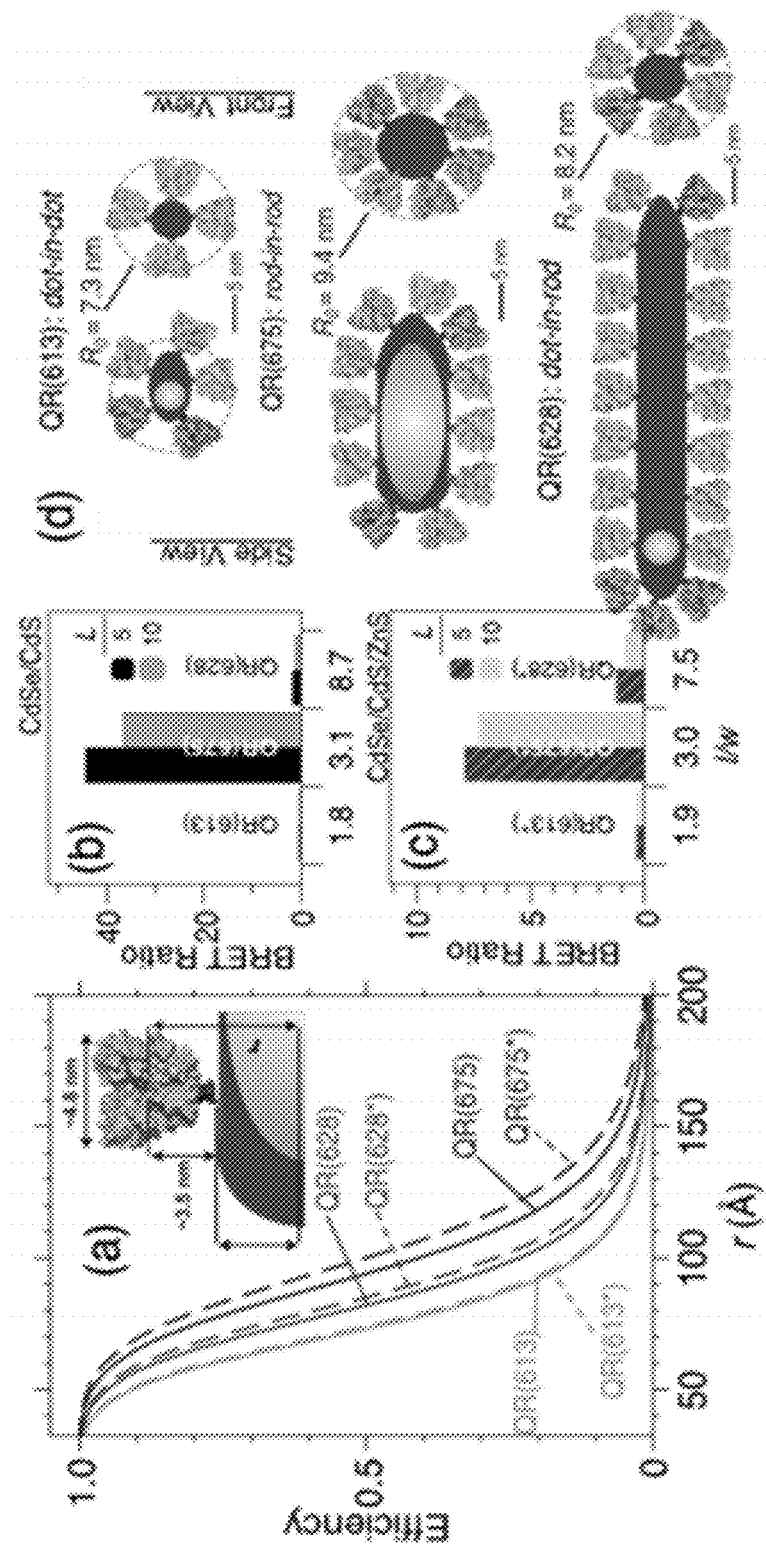

By comparison, the R$_0$ of 8.2 and 7.3 for QR(628) and QR(613), results in decreased efficiency ranges. The addition of the ZnS layers slightly changes the absorption profile of the QR, increasing R$_0$ due to higher J-values, as represented by the dashed lines in FIG. 5(a) and set forth in Table 2 below. This is offset, however, due to the increased r from the ZnS shell, which results in decreased BR for each. As an example, consider the CdSe/CdS QR(675) and CdSe/CdS/ZnS QR(675*) shown in FIGS. 2(a) and 2(b), respectively. The LH$_2$ binding site at Ppy is located ~3.5 nm from the (His)6 N-terminus of PPy, and since the radius of the QR(675) is ~4.1 nm, the shortest donor-to-acceptor distance can be approximated as r~7.6 nm, as seen in the inset of FIG. 5(a). At this r, a BRET efficiency of ~92% is expected for the PpyGRTS, and thus the high measured BR. The added 0.5-1.1 nm from the ZnS shell thus increases r, resulting in the loss of BRET efficiency.

In addition to spectral considerations, the BRET characteristics observed also indicate that QR morphology plays a critical role in influencing energy transfer parameters, as seen in FIG. 5(d). The first way is related to the number of PpyGRTS donors at each QR. For example, at aspect ratio of l/w=3.1, each QR(675) has a surface area ~750 nm$^2$, allowing it to accommodate ~42 PpyGRTS/QR (Ppy=~18 nm$^2$ footprint). The longer QR(628) at l/w=8.7 has a surface area of ~983 nm$^2$, and can accommodate up to ~55 PpyGRTS/QR. On the other hand, the QR at low aspect ratio of l/w=1.8 has surface area of ~216 nm$^2$, and can only load ~12 PpyGRTS/QR. Thus, the rods are able to accommodate more Ppy donors, compared to previously reported PpyFluorophore, and Ppy-QD examples in which the acceptor/donor ratios are 3 and 10, respectively. However, as summarized in FIG. 5(b)-(c), the BRET efficiency does not necessarily increase with aspect ratio (or loading), but instead shows a considerable maxima with QR(675) at l/w=3.1. Since each QR can accommodate 5 PpyGRTS, this suggests that the rod microstructure must also be considered when describing the BRET. It is known that the QR emission originates at the CdSe core, and that the core of these QRs is asymmetrically positioned roughly one third of the rod distance. With this in mind, the PpyGRTS distance to the core must be considered, since the PpyGRTS located furthest from the core, particularly those at r>>R0, will not participate in BRET. This is particularly important in the present invention, as while all the QRs in the present system have the same composition and general core/shell rod morphology, there are differences in the internal microstructure that are the result of the synthetic parameters.

This is illustrated in FIG. 5(d), in which each QR is shown at scale. For instance, the CdSe/CdS QR(675) with the highest efficiency was synthesized using rod-like CdSe cores (l/w=2.4±0.3, see methods), upon which longer core/shell rods were grown. Thus, it is these rod-in-rod morphologies that provide the highest efficiencies. A calculation of the average r distance $_{(rAve)}$ of the PpyGRTS from the core yields r=9.2 nm, which is close to R0 (9.4 nm). The longest QR(628) with l/w=8.7, on the other hand, used smaller and more spherical cores (d=3.9 nm), and thus the rods posses a dot-in-rod morphology. Considering the length of the rod, this results in a $_{rAve}$ z 19.2 nm, well beyond the R0 (8.2 nm). Finally, the QR(613) with l/w=1.8 has a more traditional dot-in-dot morphology, with the calculated $r_{Ave}$=8.8 nm being larger than R0 (7.3 nm). Despite these analyses, it is still unclear as to why BRET efficiency is optimized at L=5. It may be possible that some preferential histag binding occurs at the interface located close to the CdSe core, as those regions have been shown to be defect rich. It may also be possible that accessibility to substrates decreases at higher coverage, or cooperative effects result in quenching of bioluminescence. It is also important to note that very recently it was shown that QRs with rod-in-rod morphologies have improved donor properties in FRET studies with fluorophores, providing further evidence that these morphologies have importance in energy transfer. The present invention could thus be further explored by delineating the BRET efficiency using QR with similar rod-in-rod morphologies of different aspect ratios and spectral characteristics.

The present invention of quantum rods conjugated with the firefly *P. pyralis* luciferase variant PpyGRTS have high BRET ratios that are dependent upon enzyme loading, rod aspect ratio, and donor-to-acceptor distances. Moreover, and optimum loading of ~5 was demonstrated, with QRs of aspect ratio of ~3 that have rod-in-rod internal microstructure possessing the highest BRET efficiency of 44. Considering that such morphologies allow for a considerable red shift in QR emission, the present invention may be useful for optimizing NIR emission in future applications ranging from night vision capabilities to in-vivo imaging.

Figure 6:
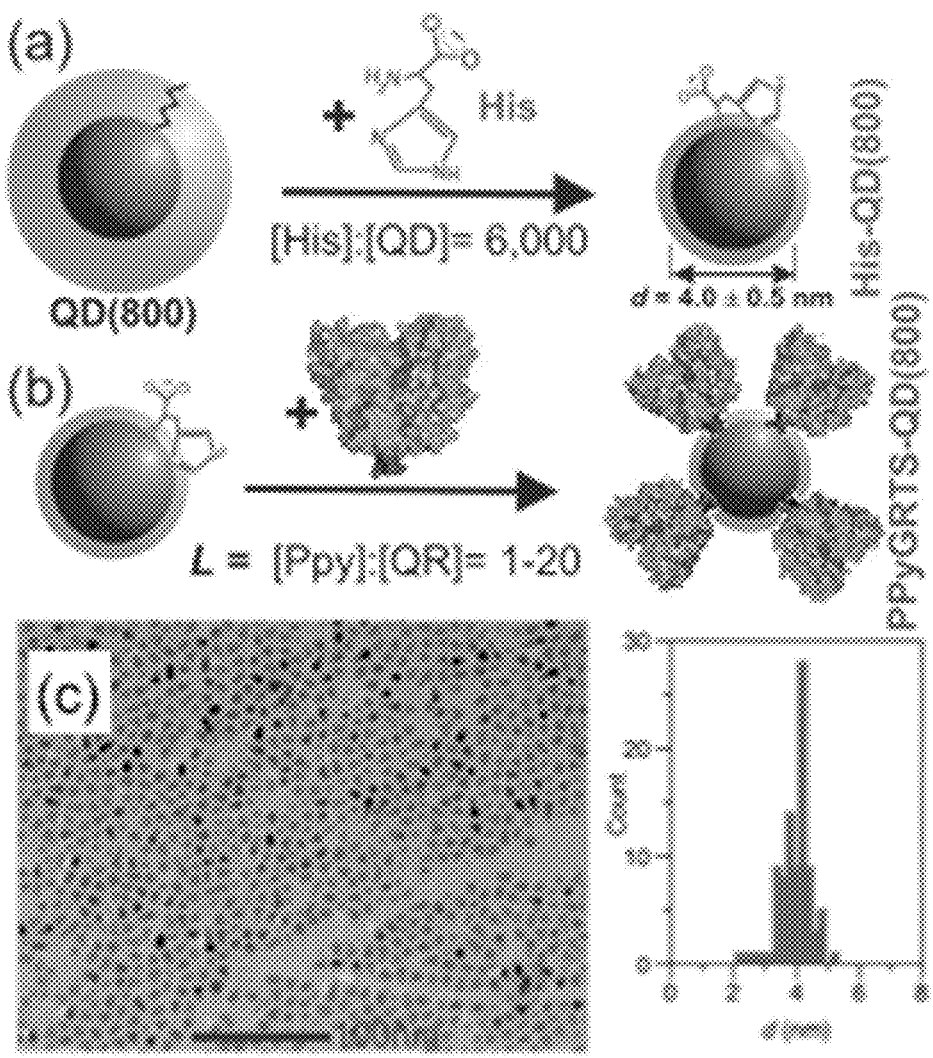
Figure 20:
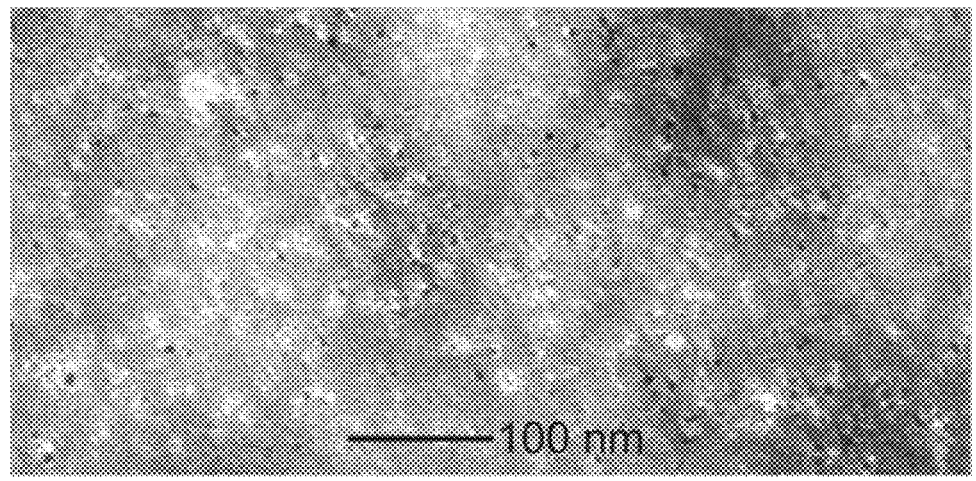
FIG. 20 is a micrograph of PpyGRTS-QD(800) conjugates at L=2 after negative staining with phosphotungstic acid.

The present invention may also be used to create BRET between PpyGRTS and near infrared (nIR) QD emitters, in which BR of 5~6 are routine. The general QD functionalization process is outlined in FIG. 6(a)-(b) using alkyl-modified hydrophobic QD(800) nIR QDs purchased commercially. Next, the QD(800) were phase transferred to aqueous buffers using the histidine (His) mediated phase transfer route. This renders the QD(800) colloidally stable in buffers, and offers a His-capping that has been shown to be facile towards biofunctionalization. The stability was illustrated by a measured quantum yield (QY) of the QD(800) of 47% in buffers, and long, single exponential, lifetimes of t=77.8±1.5 ns. Next, the His-capped QD(800) were purified free of excess His by precipitation, and incubated with PpyGRTS at increasing loading ratios, L=[PPyGRTS]/[QD(800)]=0.5-40. The PpyGRTS were coordinated to the QD interface using the Mattoussi method, which due to the presence of the N-terminus hexahistidine tag (6xHis), coordinate to the highly ionic QD interface. This attachment allows for the shortest possible donor-acceptor distance. FIG. 6(c) shows a transmission electron microscopy (TEM) micrograph of the QD(800), d=4.0±0.5 nm. The PpyGRTS functionalization was also observed by TEM using negative staining, as shown in FIG. 20.

Figure 7:
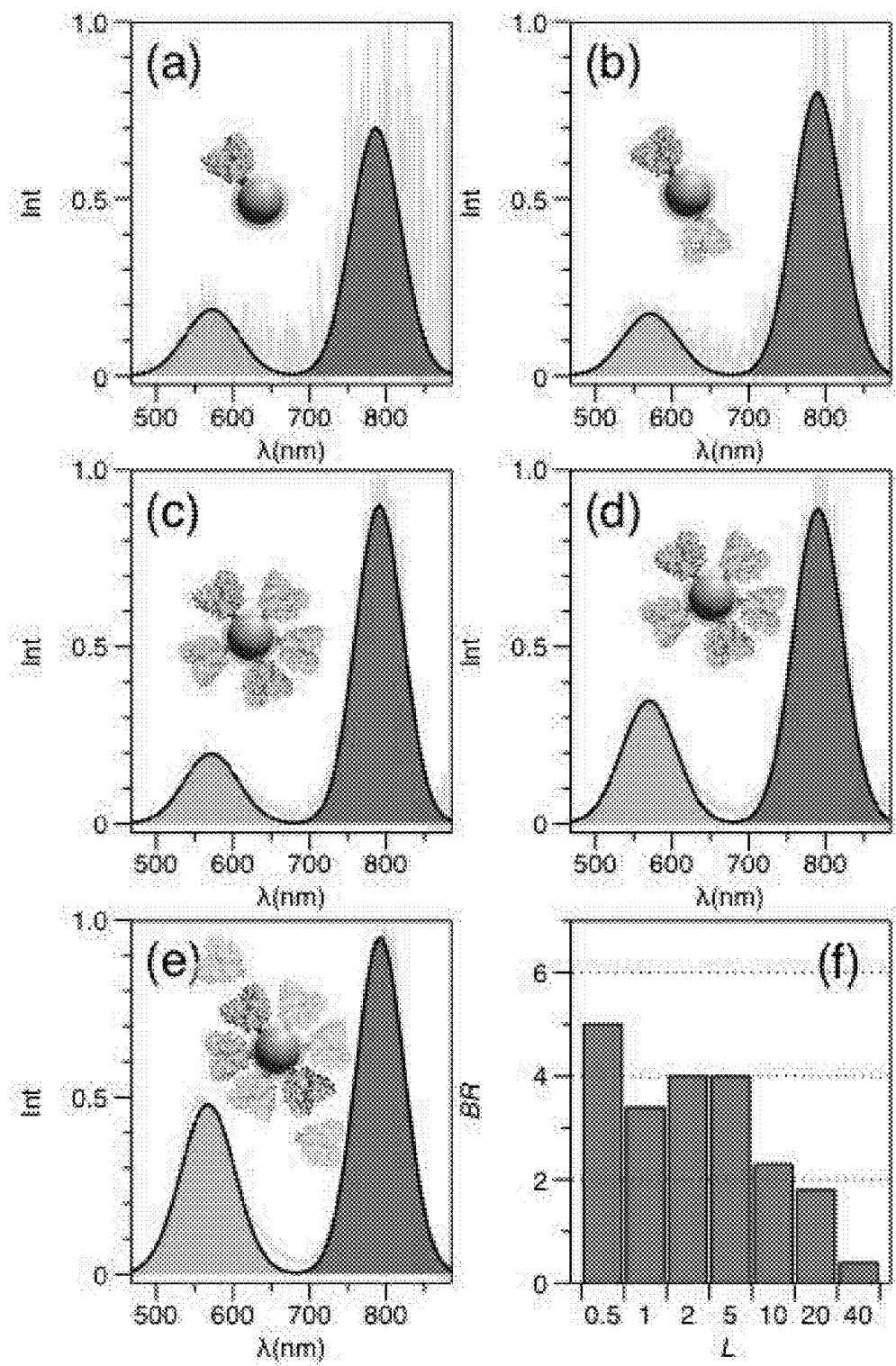
Figure 21:
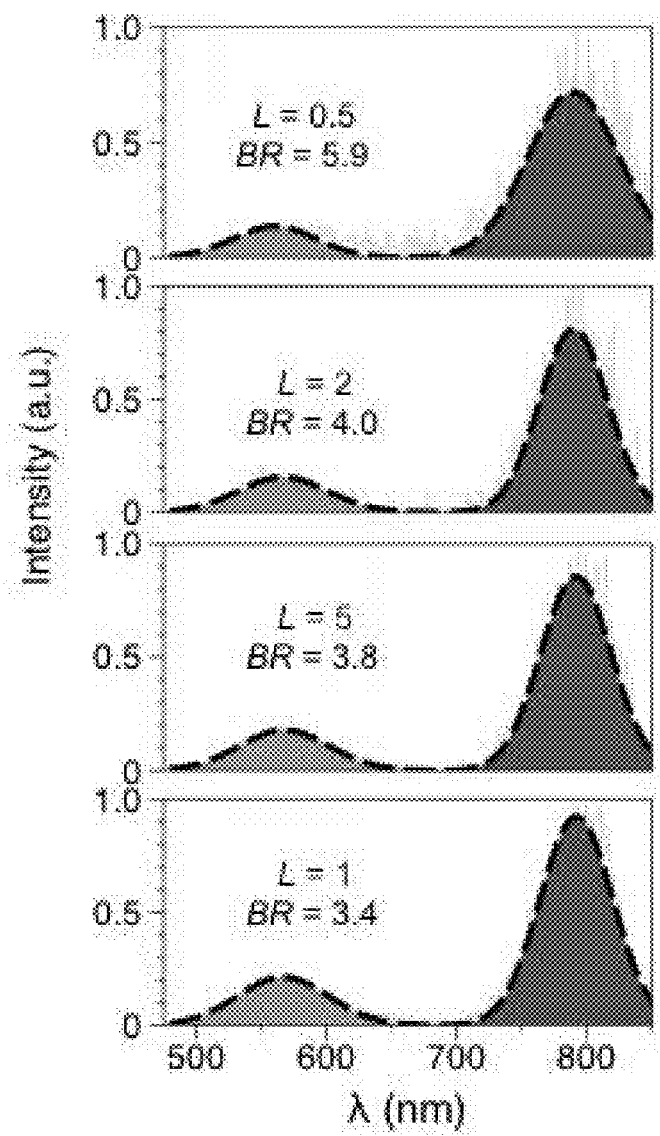
FIG. 21 is a series of graphs of the BRET emission spectra between PpyGRTS and QD800 at L=0.5, 2, 5, 10.

Upon addition of the substrate LH$_2$ to the PpyGRTS-QD (800) conjugates, we interestingly observed little to no visible light, suggesting the efficient energy transfer into the nIR. FIG. 7 quantifies this energy transfer, and shows a typical set of BRET emission results at L=0.5 (a), 1 (b), 2 (c), 5 (d), and 10(e). A characteristic feature of this data is the donor emission undergoing a Stokes shift of 249 nm, the absence of other external excitation, and the substrate based activation. The BRET efficiency was quantified by calculating the so-called BRET ratio (BR), in which the integrated emission of the acceptor (QD(800)) is divided by the integrated emission of the donor (PPyGRTS). For example, at L=1.0, as seen FIG. 2(b), a BR of 5.0 was measured. Interestingly, this BR slightly fluctuates between 4~5 from L=0.5-5.0, then drops to ~2 at L>5, as seen in FIG. 7(f). The observation of high BR at L=0.5, in which theoretically each QD(800) does not contain a bound PPyGRTS is a unique phenomena for BRET systems, since the unbound QD(800) are dark, which is reflected in the low intensity of emission (noise, as seen in FIG. 7(a)), despite identical [Qd(800)] across the samples. This phenomena also arises due to a small degree of uncertainty in regards to both the molar concentrations of QD(800) and PpyGRTS which were estimated here based on literature values for extinction coefficients. It is important to note that multiple repeat experiments resulted in similar BRET efficiencies, as seen in FIG. 21.

Figure 8:
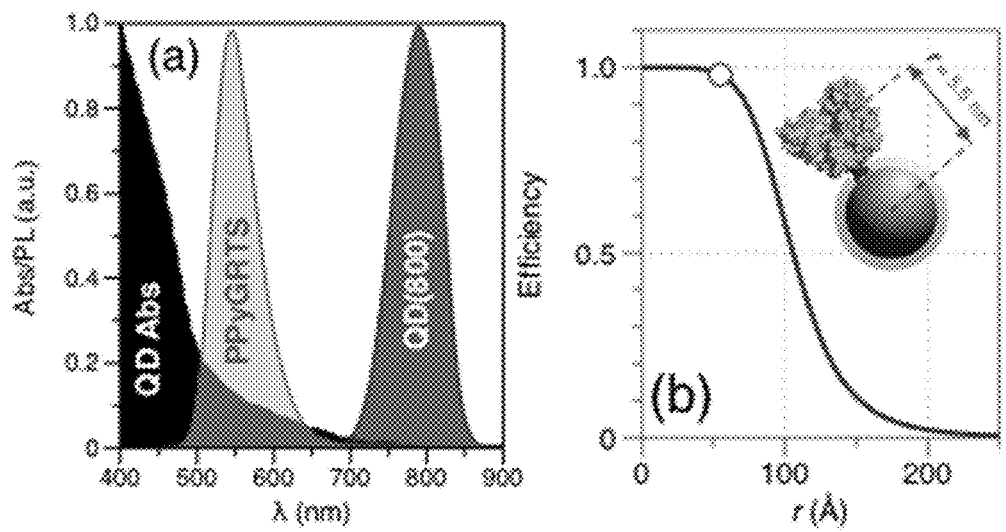

To better understand these results, the spectroscopic properties were compared, as seen in FIG. 8. Since the QD(800) has a first absorption maximum of ~790 nm, it has a significantly broad absorption profile that covers the visible spectrum and has a high extinction coefficient ($\epsilon$=2.0×10$^6$ M$^{-1}$ cm$^{-1}$ @ 550 nm). As a result, the calculated spectral overlap integral, J, is 2.37×10$^{-11}$M$^{-1}$ cm$^3$. In combination with the PPyGRTS donor QY of 32%, this results in a Förster distance (R$_0$) of 10.6 nm, one of the highest R$_0$ values used to date. If the QD(800)'s are treated as spherical, the maximum distance between the QD core, to the active site on the PPyGRTS, is r~5.5 nm, a value well below the R$_0$, as seen FIG. 3(b), and one that theoretically should result in a ≈97% efficiency under ideal conditions. In addition, since the surface area of the QD(800) is ~50 nm$^2$ and the footprint of the PpyGRTS is ~18 nm$^2$, the maximum L on each QD is 2~3, right in the range in which we observe highest BR. Due to saturation at L>5, free PPyGRTS undoubtedly remain free in solution, thus decreasing BR. One interesting consideration is that despite the large R$_0$, and the presumably low r, the BR values are not higher. When comparing these results to others that use QDs with a more or less spherical morphology, the observed BR in this study are indeed higher. For instance, the observed BR of 5.0 is 2~3× higher than CdSe/CdS core/shell QDs with identical His-capping and PPyGRTS donor recently reported. However these values are much lower than the state of the art BRET nanosystems that use QRs with rod-in-rod morphology. It is plausible that with a nIR rod-in-rod QR similar efficiencies could be achieved. The longer lifetimes of the nIR dots as compared to the CdSe/CdS rods (t≈15 ns) may also be introducing a bottleneck in the system as well. Finally, the measured BR are likely also affected by the resolution/sensitivity of the photodetector used in this study, which was corrected for wavelength sensitivity, but was undoubtedly at the end of its useful range.

Figure 9:
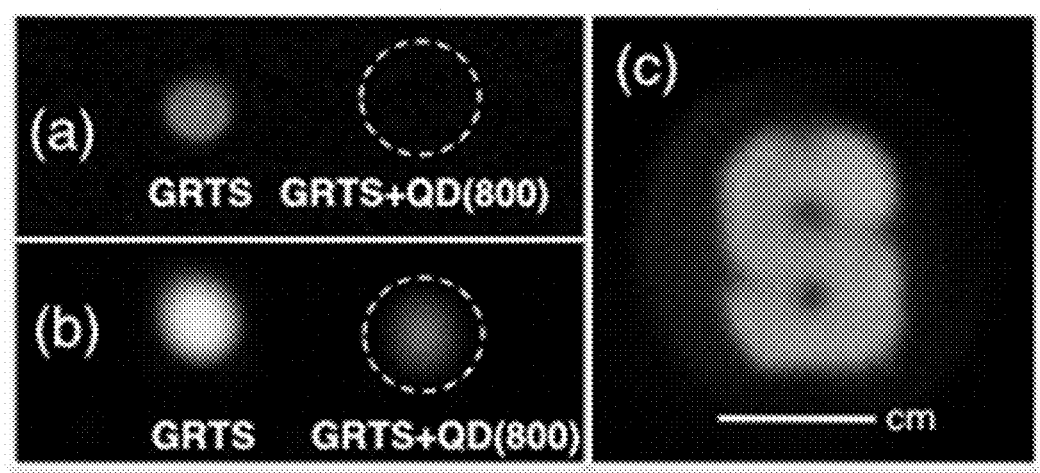

Nevertheless, BR of 5.0, and emission at 800 nm, this BRET nanosystem according to the present invention is easily observed via nIR imaging. As seen in FIG. 8, digital images were collected using a home-built set-up using commercially available night vision goggles. For example, FIG. 9(a) shows a digital image of a 98-well plate containing the PpyGRTs and PpyGRTS-QD(800) systems collected using a traditional digital camera. Only a faint GRTS spot can be observed using the concentration and conditions, and no light is detected from the GRTS-QD800 conjugate due to BRET. The identical system can be observed easily however using night vision, FIG. 9(b), in which the GRTS-QD800 is now clearly visible. This system is fully scalable, and the emitted light is related to concentration. This is illustrated by FIG. 9(c), in which a large Syracuse University logo was prepared via PDMS is filled with GRTS-QD800.

Thus, the present invention provides a mechanism for directly attaching firefly P. pyralis luciferase variants (PpyGRTS) to nIR emitting QDs. Due to the high spectral overall provided by the nIR acting as the energy acceptor, high BRET efficiencies have been observed. The BRET ratios of 4-5 were measured using loading ratios of 0.5-2, making this one of the highest efficient BRET nanosystem. The resulting nIR emission is invisible to eye, but easily observed via night vision (i.e., nIR) detectors opening up this work to contribute to the fields of in-vivo imaging as well as broader scale signaling and sensing, each of which take advantage of the chemical substrate fuel.

Example

Chemicals & Materials

Cadmium oxide (CdO, 99.99%), trioctylphine (TOP, 90%), trioctylphine oxide (TOPO, 90%), octadecene (ODE, 90%), methylphosphonic acid (MPA, 98%), sulfur (S, 100 mesh), zinc acetate ($ZnAc_2$, 99.99%), octylamine (99%), olelyamine (90%), L-histidine (His, >99.8%), sodium borohydrate ($NaBH_4$, >96%), sodium tetraborate (99.5%), boric acid (>99.5%), toluene (≥99.5%), chloroform (>99.8%), methanol (>99.8%), acetone (99.5%) were purchased from Sigma Aldrich. Selenium (Se, 200 mesh 99.99%) was purchased from Alfa Aesar. Octadecylphosphonic acid (ODPA, 98%) and hexylphosphonic acid (HPA, 98%) were purchased from Strem Chemicals. Ultrapure water (18.2 MΩ) was provided from a Sartorius Stedim Arium 61316 reverse osmosis unit combined with an Arium 611DI polishing unit. The Mg-ATP (bacterial source) was purchased from Sigma-Aldrich, and restriction endonucleases from New England Biolabs (Beverly, Mass.). Firefly luciferin ($LH_2$) was a generous gift from Promega (Madison, Wis.).

Ppy Expression

The Ppy WT was expressed as a GST-fusion protein and purified by affinity chromatography and stored. The plasmids for 6×His-Ppy GRTS was constructed by excising the corresponding genes for Ppy GRTS from the pGEX-6P-2 vector and ligating them into a modified pQE30 expression vector using previously described procedures. The His-tagged proteins were expressed, purified and stored using procedures described elsewhere. The found molecular masses (Da) of the proteins not previously reported were within the allowable experimental error (0.01%) of the calculated values (in parenthesis): 6×His-Ppy GRTS, 61 996 (62 002).

Protein concentrations were determined with the Bio-Rad Protein Assay system using BSA as the standard. DNA sequencing to verify the ligations was performed at the W. M. Keck Biotechnology Laboratory at Yale University.

Specific activity and steady state kinetics measurements were determined except that the final $LH_2$ concentration was 0.3 mM and integration times were 15 min. Bioluminescence emission spectra were obtained using methods and equipment previously described. Mass spectral analyses were performed by tandem HPLC-electrospray ionization mass spectrometry (LC/ESIMS) using a ThermoFinnigan Surveyor HPLC system and a ThermoFinnigan LCQ Advantage mass spectrometer and previously developed conditions for protein mass determinations.

Quantum Rod Synthesis:

Quantum Rods with Dot-in-Dot (D/D) Morphology (CdSe/CdS(613))

CdSe QDs were synthesized following traditional methods with slight modification. In a typical synthesis, CdO (0.06 g, 0.47 mmol), TOPO (3.00 g, 7.7 mmol), ODPA (0.28 g, 0.84 mmol) and 2 mL of ODE were mixed and heated to 150° C. under vacuum for 1 hour. Then, in an inert atmosphere, the reaction mixture was heated to 330° C. in order to dissolve CdO. When the solution changed from red-brown to clear and colorless, the temperature was increased to 360° C. Once the temperature stabilized an injection of Se (0.05 g, 0.63 mmol) and TOP (1.5 mL) was prepared in the glove box and injected into the reaction mixture. The reaction mixture was allowed to anneal for 10 minutes, then finally cooled to room temperature. In order to prevent solidification, a small amount of toluene was added at 60° C. The QDs were then purified free of excess ligands via multiple methanol extraction and precipitations. This process was repeated twice, and the final QD product was dried and dispersed in toluene. The approximate QD size and concentration was calculated as described below. The QD had PL emission centered at 602 nm, and the cores are denoted as CdSe(602).

Figure 10:
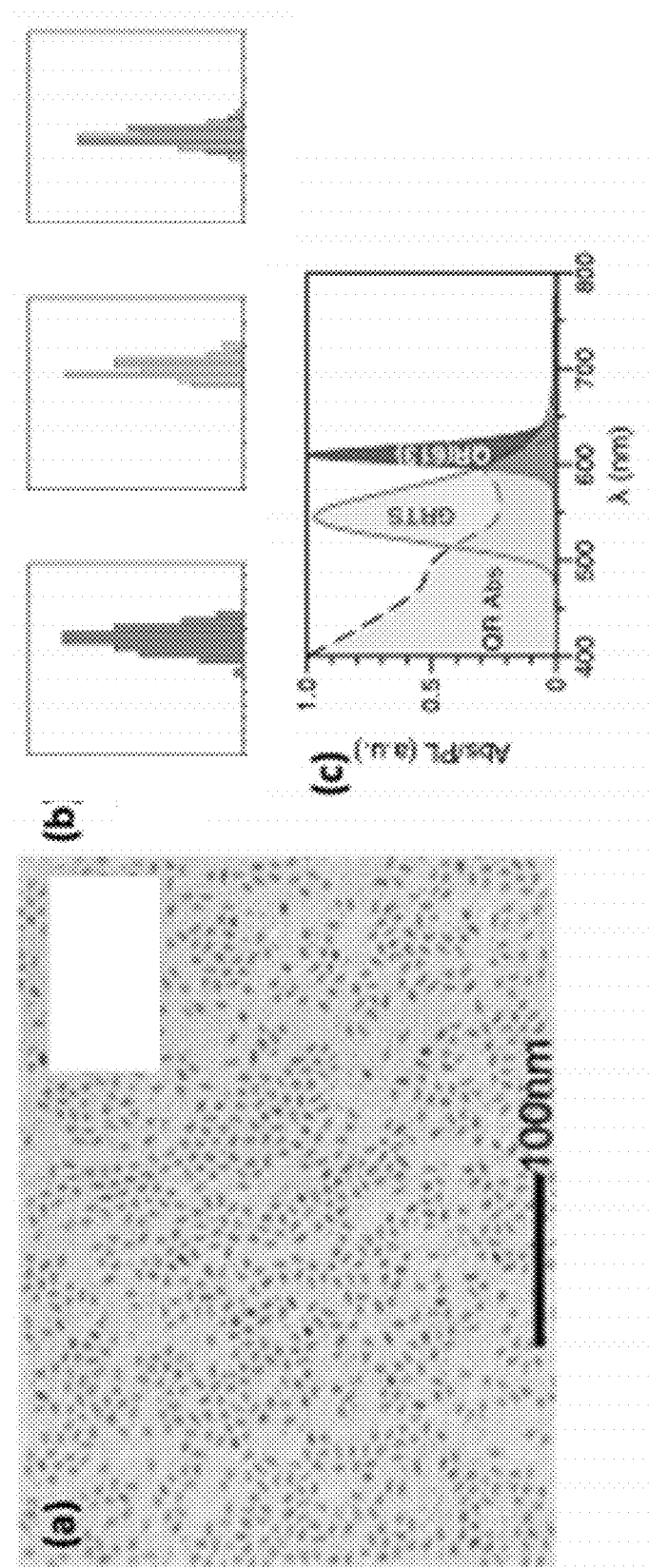

For rod growth, recent advances in methodology was applied (S8). For CdS shell deposition and rod growth on CdSe(602), the toluene was removed from the CdSe QDs via rotary evaporation and the QDs were dispersed in 5 mL of ODE and heated to 200° C. under inert atmosphere in a four-neck round-bottom flask. TOPO (0.5 g, 1.3 mmol) and oleylamine (0.75 mL, 2.3 mmol) were added to the mixture in order to limit CdSe QD growth. Then calculated amounts of cadmium precursor (0.2 M $CdAc_2$ dissolved in octylamine) and sulfur precursor (0.2 M S dissolved in ODE) were injected sequentially, waiting 10 minutes between injections to allow for shell growth. After the final injection, CdSe/CdS(613) were annealed for 30 minutes. Finally the reaction mixture was cooled to room temperature and purified in the same manner as the CdSe QDs. The resulting CdSe/CdS (613) QR are characterized in FIG. 10.

Quantum Rods with Dot-in-Rod (D/R) Morphology (CdSe/CdS(628))

Figure 11:
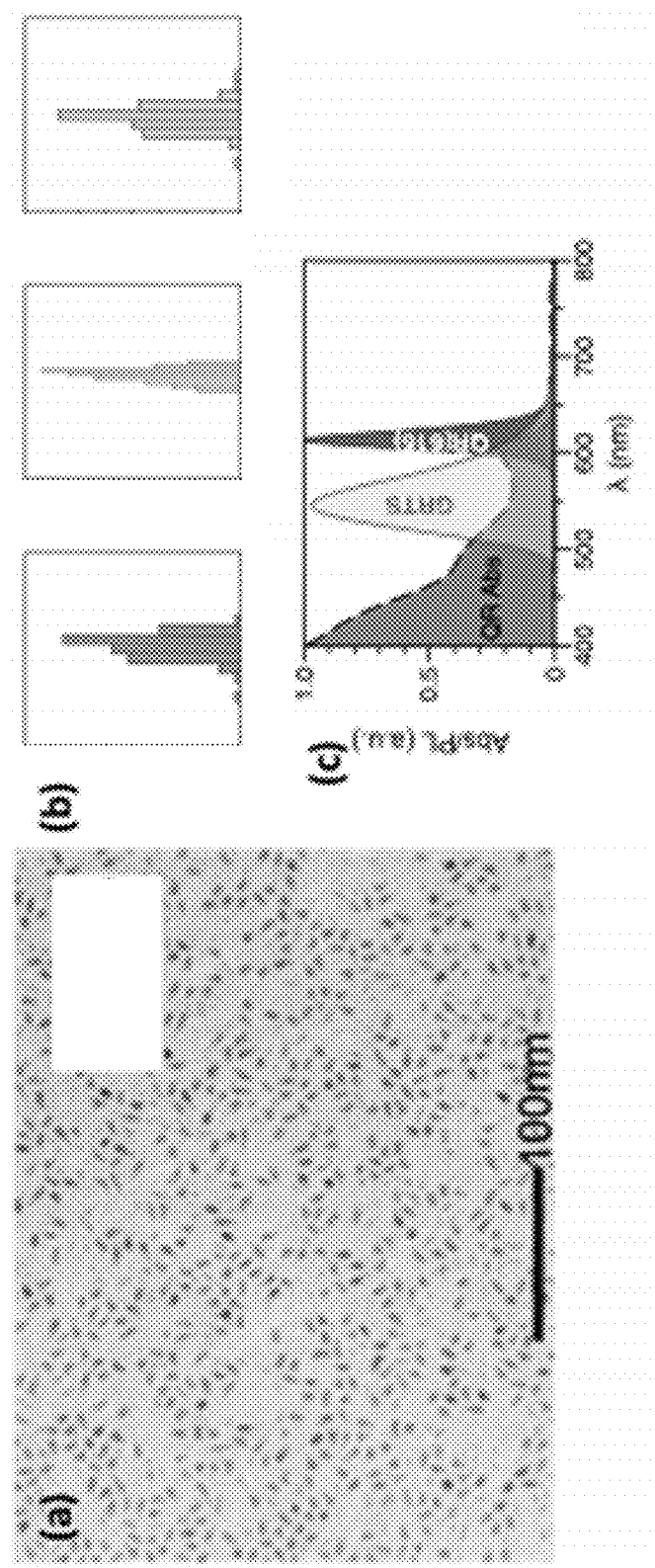
Figure 12:
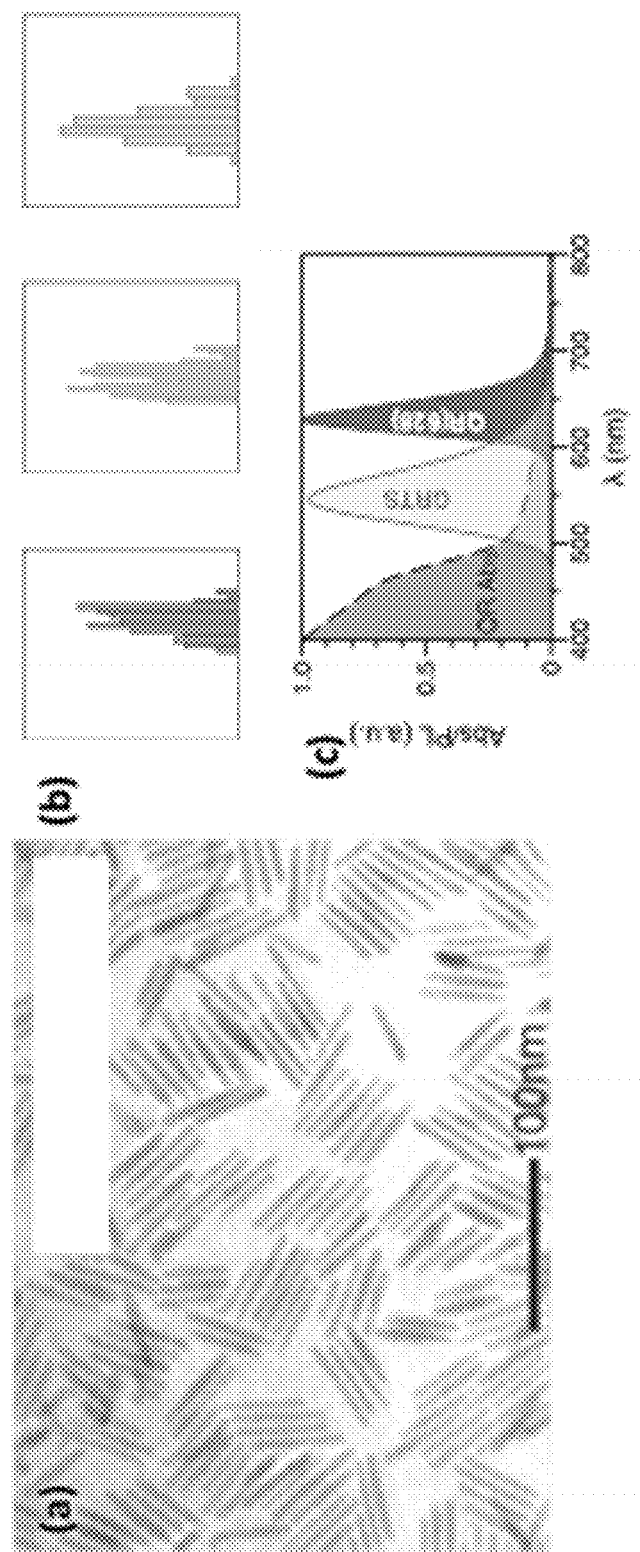

CdSe QD cores were synthesized similarly to the CdSe QD described above with minor changes. The selenium precursor was injected at 370° C., then reaction mixture was taken off the heating mantle and cooled to room temperature as soon as a color change was observed, resulting in smaller QDs (d=3.9 nm). The QD cores were then purified as described above, and used for CdS rod shell was grown. In a typical experiment, a 25 mL four neck flask was filled with CdO (0.06 g, 0.47 mmol), TOPO (3.00 g, 7.7 mmol), ODPA (0.28 g, 0.84 mmol), HPA (0.08 g, 0.48 mmol) and 2 mL of ODE and heated to 150° C. under vacuum for 1 hour. Then in an inert atmosphere, the reaction was heated to 330° C. until the solution turned clear and colorless, then the temperature was increased to 370° C. Once the temperature stabilized a mixture of $8 \times 10^{-8}$ moles of dried CdSe QDs and sulfur (0.12 g, 3.7 mmol) dissolved in 2.0 mL of TOP in the glove box and quickly injected into the reaction mixture and annealed for 10 min. The resulting CdSe/CdS(628) QR with dot-in-rod morphology are characterized in FIG. 11.

Quantum Rods with Rod-in-Rod (R/R) Morphology (CdSe/CdS(675)

Figure 14:
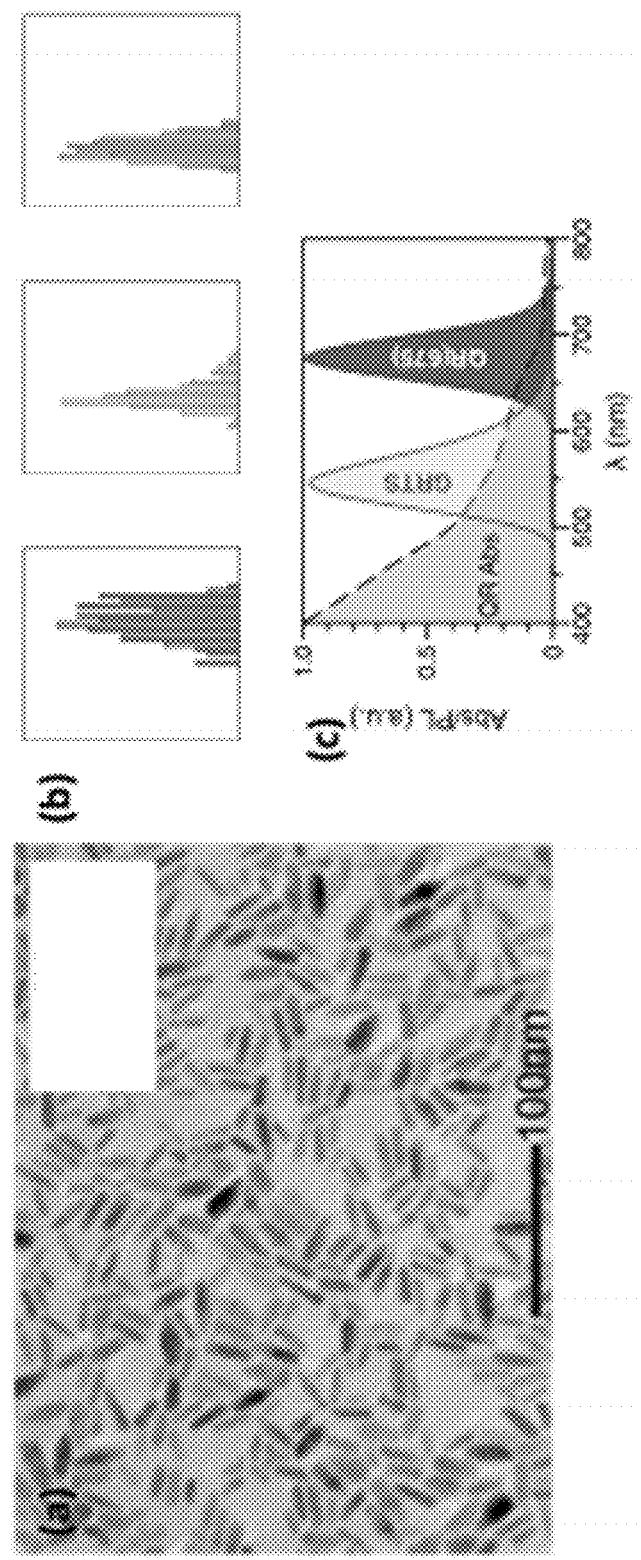

First, CdSe cores with rod morphology were synthesized. In a typical experiment, a mixture of CdO (0.06 g, 0.47 mmol), TOPO (3.00 g, 7.7 mmol), ODPA (0.24 g, 0.72 mmol), MPA (0.01 g, 0.10 mmol) and 2 mL of ODE in a four-neck round-bottom flask was heated to 150° C. under vacuum for one hour. Then the reaction mixture was placed under argon and the temperature was increased to 330° C. in order to dissolve CdO. When the solution changed from red-brown to clear and colorless, the temperature was raised to 365° C. Then 0.5 mL of TOP was injected. Once the temperature stabilized at 365° C., an injection of Se (0.05 g, 0.63 mmol) dissolved 1 mL of TOP prepared in the glove box, was swiftly injected into the reaction mixture and annealed for 10 minutes. Finally the reaction solution was cooled to room temperature. In order to prevent solidification, a small amount of toluene was added at 60° C. then cleaned and dispersed in toluene. The resulting CdSe rod cores had an aspect ratio of l/w=2.4±0.3. For growth of the CdS rod shell, CdO (0.03 g, 0.23 mmol), TOPO (3.00 g, 7.7 mmol), ODPA (0.14 g, 0.42 mmol), HPA (0.04 g, 0.24 mmol) and 2 mL of ODE were mixed and heated to 150° C. under vacuum for 1 hour. Then in an inert atmosphere, the reaction was heated to 330° C. until the solution turned clear and colorless, then the temperature was increased to 365° C. Once the temperature stabilized, a solution of $1 \times 10^{-8}$ moles of dried CdSe QRs and sulfur (0.06 g, 1.9 mmol) dissolved in 2.0 mL of TOP in the glove box and quickly injected into the reaction flask. For the growth of CdS shell, the reaction mixture was annealed for 10 minutes after the injection. Next the QRs were cooled to room temperature and treated the same way as CdSe seeds. The resulting CdSe/CdS(675) QR with rod-in-rod morphology are characterized in FIG. 14.

ZnS Shell Growth on QRs.

Figure 13:
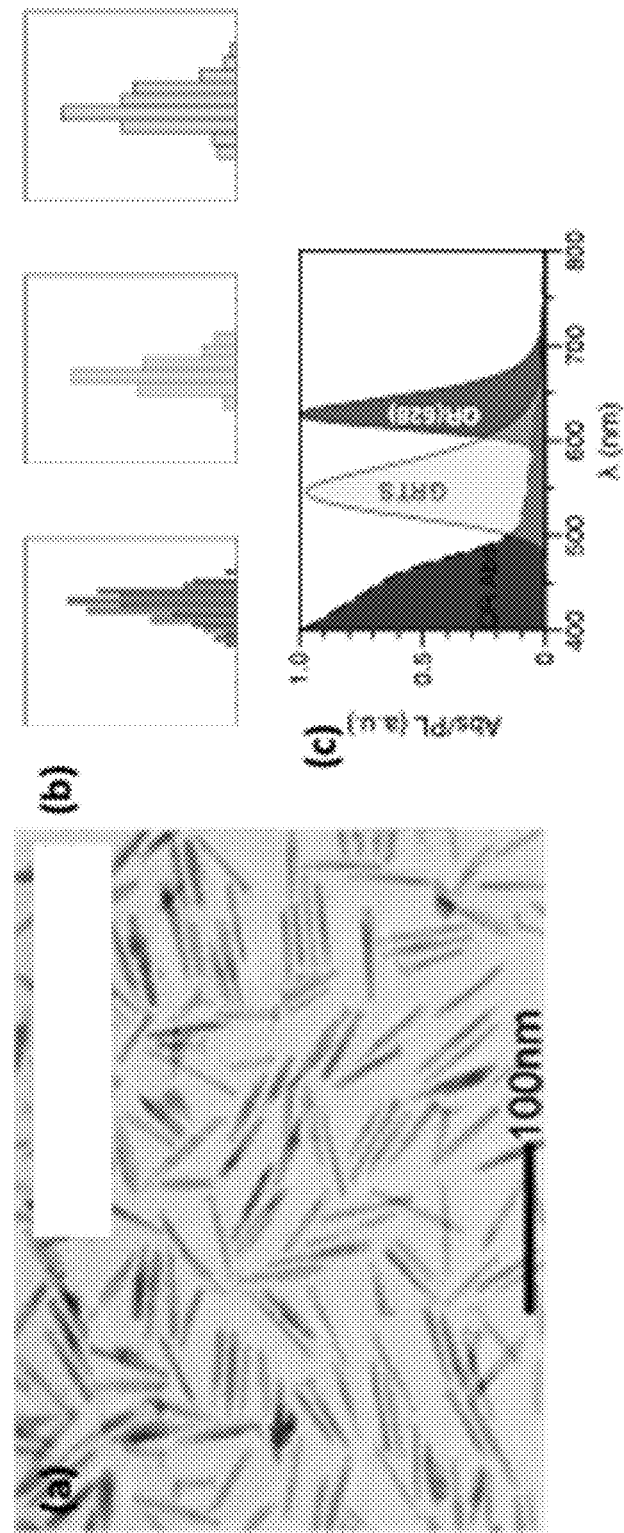
Figure 15:
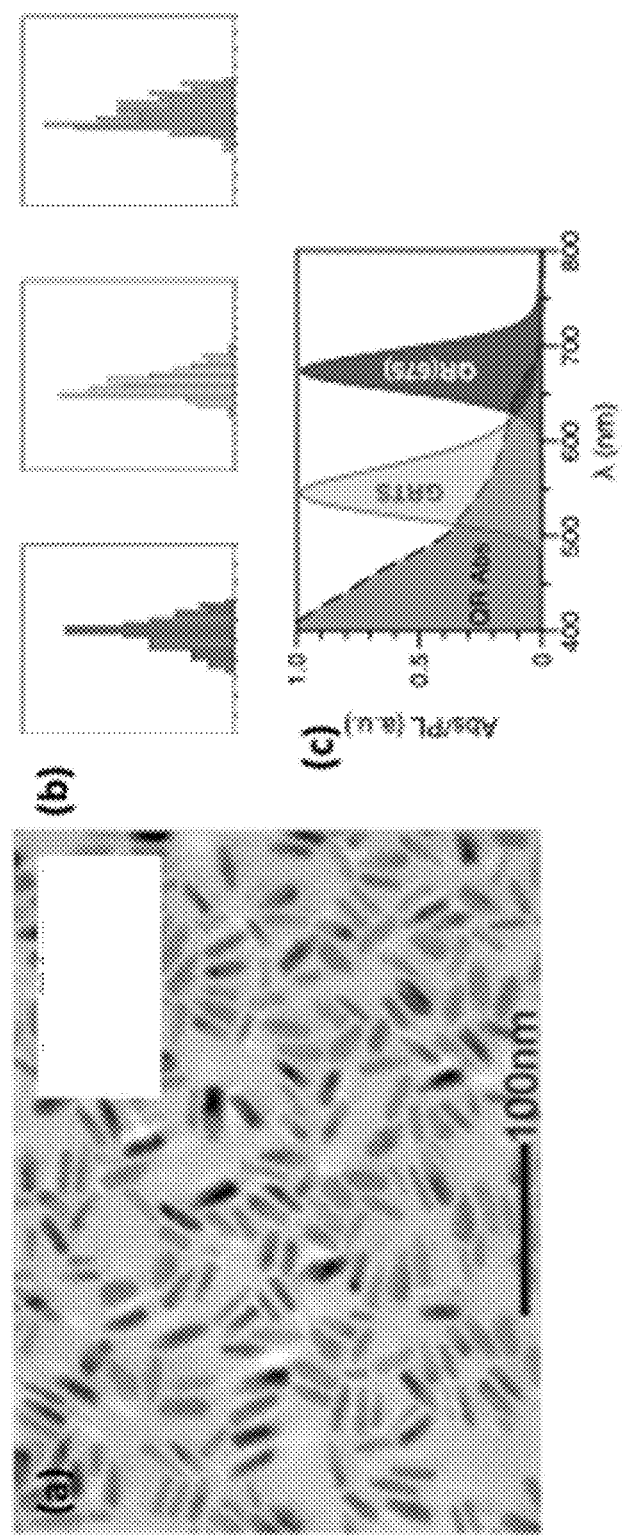
Figure 16:
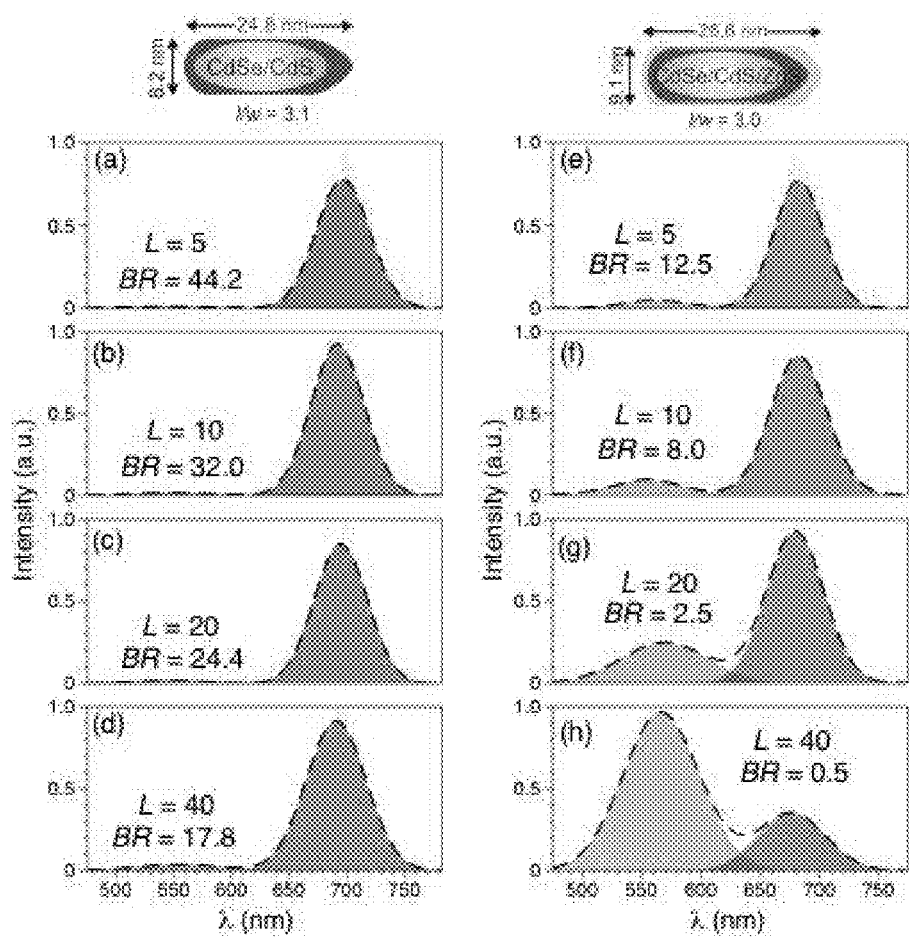
Figure 17:
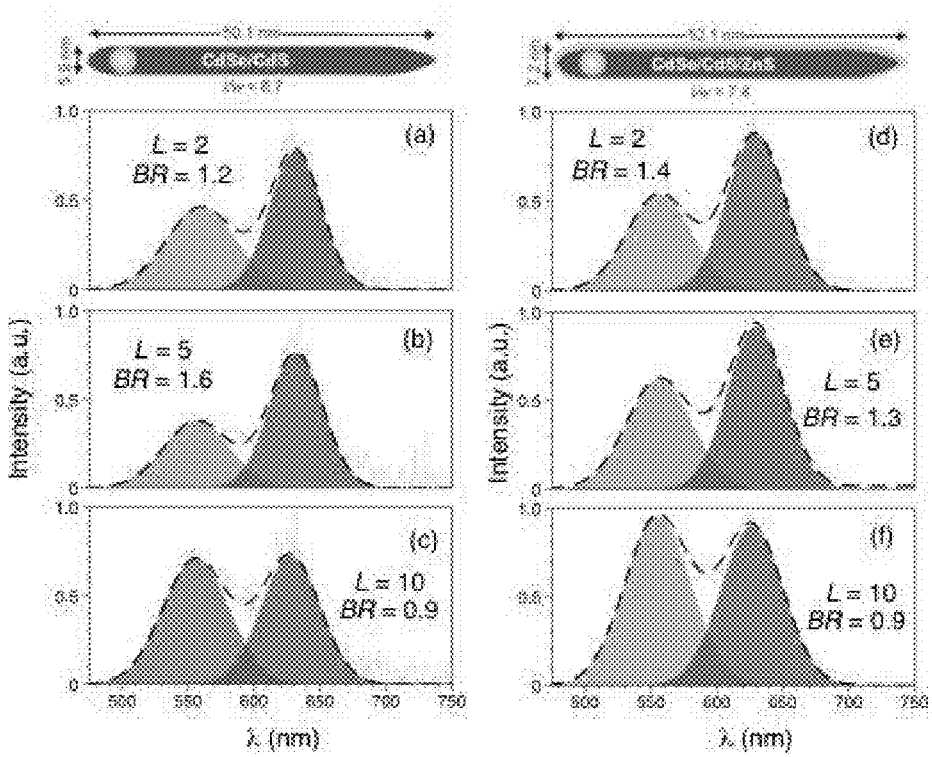
Figure 18:
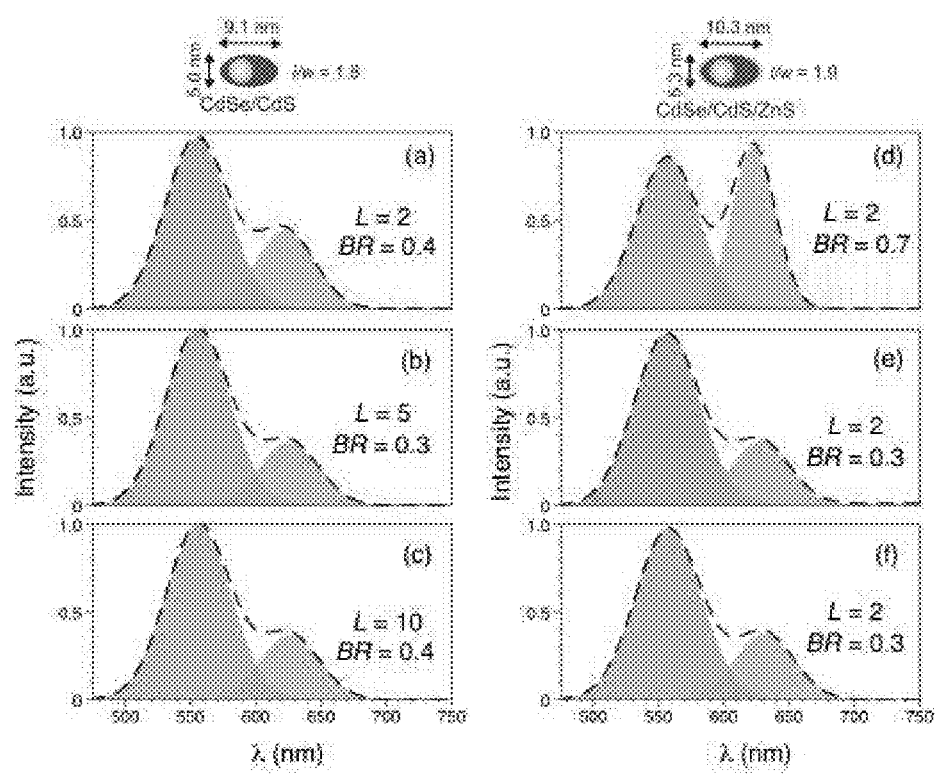
Figure 19:
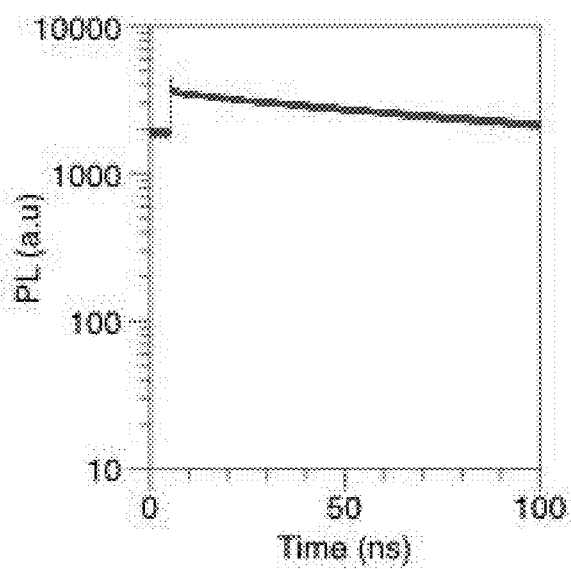
FIG. 19 is a graph of the PL decay spectra of QD800. Single exponential fit to the data gives lifetime of $\tau=77.8\pm1.5$ ns.

For each of the QR synthesized above, and additional thin layer of ZnS could also be grown following the SILAR approach. This was achieved at 200° C. in a mixture of QRs, TOPO (1.0 g) and ODE (5.0 mL). The zinc precursor (0.2 M $ZnAc_2$ dissolved in octylamine) and sulfur precursor (0.2 M S dissolved in ODE) were injected slowly and sequentially, 100-200 μl injections at a time waiting 10 minutes between injections. After the final injection, the reaction mixture was allowed to anneal for 30 minutes. The total volume of precursor used was calculated based on the size of the QRs and the desired shell thickness. The resulting CdSe/CdS/ZnS QRs are characterized in FIGS. 11, 13 and 15.

Histidine-Mediated Phase Transfer

In order to phase transfer the hydrophobic QRs into aqueous buffers a phase transfer technique was used. The organic ligands of the QR were directly exchanged with the small molecule L-histidine (His), rendering them hydrophilic, and both colloidally and optically stable. This histidine-mediated phase transfer method was achieved by adding a ~5000-fold [His]:[QR] molar excess. Initially a histidine solution was prepared by dissolving histidine in a basic 3:1 $MeOH/H_2O$ solution. Then, ~5000-fold excess of the histidine solution was added to cleaned QRs dispersed in chloroform and vortexed for 1 minute. This resulted in the QRs being transferred to the aqueous layer, to 10 mM borate buffer (pH 8.3). Excess organic ligands were back-extracted by addition of fresh chloroform, vortexing, and decanting of the organic solution. This extraction procedure was repeated at least four times. Then excess histidine molecules were removed by rinsing the hydrophilic QRs with 10 mM borate buffer using a 100 kDa molecular weight centrifugal filter (Millipore). Finally the QRs were dispersed in 10 mM borate buffer and refrigerated before use. The QR concentration was calculated as described below.

PpyGRTS-QR Conjugation

To construct the PpyGRTS-QR BRET nanosystems, the His-functionalized QRs were incubated with the histagged PpyGRTS in 10 mM borate buffer at loading ratios, L=[PpyGRTS]/[QR] on ice. Incubation was allowed to proceed for at least 15 minutes before BRET analysis.

Instrumentation

UV-Vis Spectrophotometry (UV-Vis).

The UV-Vis measurements were collected on a Varian Cary100 Bio UV-Vis spectrophotometer between 200 and 900 nm. The instrument is equipped with an 8-cell automated holder with high precision Peltier heating controller.

Photoluminescence (PL) and Bioluminescence

The QR PL emission and Ppy bioluminescence was collected on a Fluoromax-4 photon counting spectrofluorometer (Horiba Jobin Yvon). The instrument is equipped with a 150 W xenon white light excitation source and computer-controlled monochromator. The detector is a R928P high sensitivity photon counting detector that is calibrated to emission wavelength. All PL emission and excitation spectra were collected using both wavelength correction of source intensity and detector sensitivity. The excitation wavelength for QR quantum yield calculations was 400 nm using 3 nm excitation and emission slits unless otherwise noted. Bioluminescence spectra were collected with the excitation source blocked.

Transmission Electron Microscopy (TEM)

TEM measurements were performed on a JEOL 2000EX instrument operated at 100 kV with a tungsten filament (SUNY-ESF, N.C. Brown Center for Ultrastructure Studies). Negative staining was achieved using phosphotungstic acid. Particle size and aspect ratio were analyzed manually with statistical analysis per-formed using ImageJ software on populations of at least 100 counts.

BRET Measurement and Analysis

In a typical BRET experiment, a mixture of 100 μL of 91 μM $LH_2$ (firefly luciferin) and 30 μL of 8.66 mM Mg-ATP in 25 mM gly-gly buffer (pH 7.8) is quickly added to the Ppy-QR conjugate solution ([QR]=230-700 nM) in a 96-well plate and bioluminescence emission is immediately collected. The bioluminescence and BRET were collected on a Varian Cary-Eclipse spectrophotometer in bioluminescence/chemiluminescence mode using a 96-well plate reading accessory. White 96-well plates were employed, with volumes ranging from 50-200 mL. Bioluminescence spectra were collected every 15 seconds for 7.5 minutes. The instrument was corrected for detector sensitivity by comparison of fluorescence standard emission intensities (500-800 nm) with the corrected detector on the Fluoromax-4 spectrophotometer (see above). The presented BRET results are the average of the first five spectra collected over 1.5 min after addition of $LH_2$. Control experiments showed that the BRET ratio did not change over the course of the typical BRET decay. Additionally, control experiments showed that BRET efficiency was not influenced greatly by $[LH_2]$, but overall signals improved at high excess of $LH_2$. Finally, the BRET efficiencies of the systems were calculated as BRET ratio (BR), which is defined as the ratio of peak area of the acceptor and donor emission respectively. Peak area was calculated by spectral deconvolution of each spectrum using the data analysis package in Igor Pro (Wavemetrics Inc.).

Calculations

QD and QR Concentration

The concentrations of the QD cores were calculated based on UV-vis optical absorption measurements of the QD first band edge absorption (1s-1s) intensity using QD size dependent optical extinction coefficients ($\epsilon$). The concentration of particles with QR morphologies was calculated based on UV-vis optical absorption at 350 nm and extinction coefficients ($\epsilon_{QR}$) based on the average volume of the QRs. The final concentrations were obtained using the Beer-Lambert equation, Abs=$\epsilon$bc; where c is the estimated extinction coefficient ($M^{-1}$ cm-1), b is the path length, and c is concentration. A tabulation of the calculated c values is given in Table 2 below.

TABLE 2

Morphological and optical properties for the quantum rods (QR) of the present invention

| Name | Type | Class[A] | Morphology | | | Optical Properties | | |
|---|---|---|---|---|---|---|---|---|
| | | | l/w | l(nm) | W(nm) | QY(%) | $\lambda_{Abs}$(nm)[B] | $\epsilon A(M^{-1}cm^{-1})$[C] |
| QR(675) | CdSe/CdS | (R/R) | 3.1 ± 0.5 | 24.8 ± 3.6 | 8.2 ± 1.3 | 23 | 632 | 791559.8 |
| QR(675*) | CdSe/CdS/ZnS | (R/R) | 3 ± 0.5 | 26.6 ± 3.8 | 9.1 ± 1.3 | 14 | 638 | 940895.7 |
| QR(628) | CdSe/CdS | (D/R) | 8.7 ± 1.6 | 50.1 ± 5.5 | 5.9 ± 0.8 | 33 | 603 | 357503.9 |
| QR(628*) | CdSe/CdS/ZnS | (D/R) | 7.4 ± 1.5 | 52.1 ± 5.8 | 7.2 ± 1.1 | 21 | 610 | 429857 |
| QR(613) | CdSe/CdS | (D/D) | 1.8 ± 0.2 | 9.1 ± 0.9 | 5 ± 0.4 | 19 | 600 | 330942.4 |
| QR(613*) | CdSe/CdS/ZnS | (D/D) | 1.9 ± 0.3 | 10.3 ± 1.3 | 5.3 ± 0.5 | 18 | 603 | 357503.9 |

Quantum Yield (QY)

The QR photoluminescence quantum yields (QY) were calculated based on comparison to a reference dye using standard methods (equation 1) (S13):

$$QY_{qdot}(\%) = QY_R \left(\frac{Abs_R}{Abs_{qdot}}\right)\left(\frac{PL_{qdot}}{PL_R}\right)\left(\frac{\eta^2_{qdot}}{\eta^2_R}\right) \quad (1)$$

where $QY_R$ is the reference dye quantum yield (Rhodamine 6G=95%), $Abs_R$ and $Abs_{QD}$ are the optical absorption at specific excitation for the reference dye and QR samples respectively. Here, careful attention was paid to prepare samples with optical absorption below 0.10 in order to limit inner filter effects. $PL_R$ and $PL_{QD}$ correspond to the total area of the PL emission after wavelength dependent calibration of both the excitation source, and photoluminescence detector, as well as after PL spectra baseline correction.

Förster Resonance Energy Transfer (FRET) Calculations

In this study, the bioluminescence resonance energy transfer (BRET) constants were calculated in the identical manner to FRET. In FRET, the Förster distance ($R_0$), in units of angstroms, is calculated using equation 2:

$$R_0=9.78\times10^3((\kappa^2 n^{-4}Q_D J(\lambda))^{1/6} \quad (2)$$

where n refractive index of the medium (n=1.33), $\kappa$ is the dipole orientation factor ($\kappa$=2/3), $Q_D$ is the donor quantum yield QY(GRTS)≈32%, and J($\lambda$) is the spectral overlap integral. The J($\lambda$) value can be calculated using equation 3:

$$J(\lambda)=\int F_D(\lambda)\epsilon_A(\lambda)\lambda^4 d\lambda, \quad (3)$$

where $\lambda$ is the defined wavelength of the donor-acceptor spectral overlap, and $F_D(\lambda)$ is the integrated donor emission with area normalized to unity, and $\epsilon_A(\lambda)$ represents the acceptor extinction coefficient at the particular wavelength.

When $\epsilon_A(\lambda)$ is in units of $M^{-1}$ $cm^{-1}$, and l is in units of cm, the units for J($\lambda$) are $M^{-1}$ $cm^3$, and equation 2 is relevant.

Using the $R_0$ values calculated above, the FRET efficiency, E, was calculated using equation 4:

$$E = 1 - \frac{F_{DA}}{F_D} = \frac{R_0^6}{R_0^6 + r^6} \quad (4)$$

where $F_{DA}$ is donor fluorescence in the presence of acceptor, and $F_D$ is fluorescence of the donor without acceptor. A tabulation of the calculated BRET constants is shown in Table 3 below:

TABLE 3

Calculated BRET constants for the Ppy-QR nanosystems

| | | PPy GRTS[A] | | |
|---|---|---|---|---|
| Name | Type | | J ($M^{-1}$ $cm^3$)[B] | $R_0$ (mn)[C] |
| QR(675) | CdSe/CdS | (R/R) | 1.19 × 10$^{-11}$ | 9.4 |
| QR(675*) | CdSe/CdS/ZnS | (R/R) | 1.65 × 10$^{-11}$ | 10.0 |
| QR(628) | CdSe/CdS | (D/R) | 5.26 × 10$^{-12}$ | 8.2 |
| QR(628*) | CdSe/CdS/ZnS | (D/R) | 6.21 × 10$^{-12}$ | 8.5 |
| QR(613) | CdSe/CdS | (D/D) | 2.49 × 10$^{-12}$ | 7.3 |
| QR(613*) | CdSe/CdS/ZnS | (D/D) | 2.77 × 10$^{-12}$ | 7.4 | where [A]PPy GRTS, QY=32%, $\lambda_D$=546 nm; [B] Calculated using equation 3; and [C]Calculated using equation 2.

What is claimed is:

1. A bioluminescent energy transfer system, comprising: a semiconductive quantum rod having a rod-shaped core surrounded by a rod-shaped shell that fluoresces at a predetermined frequency; and
at least one luciferase protein having a hexahistidine tag, wherein the hexahistidine tag binds the luciferase protein directly to the shell of the quantum rod via non-covalent coordination.

2. The system of claim 1, wherein said hexahistidine tag comprises an N-terminus hexahistidine tag.

3. The system of claim 2, wherein said luciferase comprises *Photinus pyralis* luciferase.

4. The system of claim 1, wherein said rod-shaped core comprises a CdSe rod-shaped core and said rod-shaped shell comprises a CdS rod-shaped shell.

5. The system of claim 4, wherein said quantum rod has an aspect ratio of at least 3.1.

6. The system of claim 1, wherein said quantum rod further comprises a layer of ZnS.

7. The system of claim 6, wherein said quantum rod has an aspect ratio of about 3.1.

8. The system of claim 1, wherein said predetermined frequency is in the infrared spectrum.

9. The system of claim 1, wherein said predetermined frequency is in the visible spectrum.

10. A method of emitting light, comprising the steps of:
providing a bioluminescent complex having a semiconductive quantum rod a rod-shaped core surrounded by a rod-shaped shell that fluoresces at a predetermined frequency and at least one luciferase protein having hexahistidine tag that binds the luciferase protein directly to the surface of the quantum rod via non-covalent coordination; and
exposing said bioluminescent complex to a substrate of said luciferase molecule.

11. The method of claim 10, wherein said hexahistidine tag resides at the N-terminus of said luciferase.

12. The method of claim 11, wherein said luciferase comprises *Photinus pyralis* luciferase.

13. The method of claim 11, wherein rod-shaped core comprises a CdSe rod-shaped core and said rod-shaped shell comprises a CdS rod-shaped shell.

14. The method of claim 13, wherein said quantum rod has an aspect ratio of about 3.1.

15. The method of claim 11, wherein said quantum rod further comprises a layer of ZnS.

16. The method of claim 15, wherein said quantum rod has an aspect ratio of about 3.0.

17. The method of claim 10, wherein said predetermined frequency is in the infrared spectrum.

18. The method of claim 10, wherein said predetermined frequency is in the visible spectrum.

* * * * *